United States Patent
Thomas et al.

(10) Patent No.: US 7,461,554 B2
(45) Date of Patent: Dec. 9, 2008

(54) DIGITAL TIME VARIABLE GAIN CIRCUIT FOR NON-DESTRUCTIVE TEST INSTRUMENT

(75) Inventors: Andrew Thomas, Westford, MA (US); Steven Besser, Framingham, MA (US)

(73) Assignee: Olympus NDT, Waltham, MA (US)

(*) Notice: Subject to any disclaimer, the term of this patent is extended or adjusted under 35 U.S.C. 154(b) by 340 days.

(21) Appl. No.: 11/489,892

(22) Filed: Jul. 20, 2006

(65) Prior Publication Data

US 2007/0085606 A1 Apr. 19, 2007

Related U.S. Application Data

(60) Provisional application No. 60/726,575, filed on Oct. 14, 2005, provisional application No. 60/726,798, filed on Oct. 14, 2005, provisional application No. 60/726,776, filed on Oct. 14, 2005.

(51) Int. Cl.
*G01N 29/38* (2006.01)

(52) U.S. Cl. .................. 73/602; 73/609; 73/614

(58) Field of Classification Search ............... 73/602, 73/609, 610, 611, 613, 614, 615
See application file for complete search history.

(56) References Cited

U.S. PATENT DOCUMENTS

| 4,497,210 A | 2/1985 | Uchida et al. |
| 5,490,511 A | 2/1996 | Amemiya et al. |
| 5,671,154 A | 9/1997 | Iizuka et al. |
| 5,737,238 A | 4/1998 | Mouradian et al. |
| 5,803,304 A * | 9/1998 | Berg .......................... 220/565 |
| 6,016,700 A * | 1/2000 | Cuffe ........................... 73/602 |
| 6,141,672 A | 10/2000 | Driendl et al. |
| 6,192,164 B1 * | 2/2001 | Park ........................... 382/300 |
| 6,473,182 B1 * | 10/2002 | Tazartes et al. ............. 356/464 |
| 6,474,164 B1 | 11/2002 | Mucciardi et al. |
| 6,511,426 B1 | 1/2003 | Hossack et al. |
| 6,582,372 B2 | 6/2003 | Poland |
| 6,789,427 B2 | 9/2004 | Batzinger et al. |
| 6,867,941 B1 * | 3/2005 | Ozdemir ...................... 360/66 |
| 6,963,733 B2 | 11/2005 | Eriksson et al. |
| 7,102,434 B2 | 9/2006 | Grillo |

OTHER PUBLICATIONS

Jerry E. Purcell, Ph.D., "Multirate Filter Design—An Introduction," pp. 1-15.
PCT Notification of Transmittal of International Search Report issued in connection with corresponding PCT application PCT/US06/036908 dated Aug. 14, 2007.
International Search Report dated Oct. 19, 2007 in connection with corresponding PCT Application No. PCT/US06/36810.
International Search Report and Written Opinion dated Aug. 7, 2008 relating to PCT Application No. PCT/US06/37110.

* cited by examiner

*Primary Examiner*—Hezron E. Williams
*Assistant Examiner*—Jacques M. Saint-Surin
(74) *Attorney, Agent, or Firm*—Ostrolenk Faber Gerb & Soffen, LLP

(57) ABSTRACT

In a non-destructive test instrument, there is provided a time variable gain (TVG) amplifier wherein the gain of the amplifier is dynamically changed to optimize the amplitude of a flaw echo signal. The TVG digital memory for a given TVG curve specifies and controls not only the start gain value, and the end game value, but the gain rate of change slope as well to generate TVG curve line segments.

35 Claims, 17 Drawing Sheets

DIGITAL TIME VARIABLE GAIN CIRCUIT FOR NON-DESTRUCTIVE TEST INSTRUMENT

CROSS-REFERENCE TO RELATED APPLICATIONS

This application claims the benefit and priority of U.S. Provisional patent application Ser. No. 60/726,798 filed Oct. 14, 2005 entitled ULTRASONIC FAULT DETECTION SYSTEM USING A HIGH DYNAMIC RANGE ANALOG TO DIGITAL CONVERSION SYSTEM and U.S. Provisional patent application Ser. No. 60/726,776, filed Oct. 14, 2005 entitled ULTRASONIC DETECTION MEASUREMENT SYSTEM USING A TUNABLE DIGITAL FILTER WITH 4X INTERPOLATOR, and U.S. Provisional patent application Ser. No. 60/726,575, filed Oct. 14, 2005 entitled DIGITAL TIME VARIABLE AMPLIFIER FOR NON-DETRUCTIVE TEST INSTRUMENT, the entire disclosures of which are incorporated herein by reference.

BACKGROUND OF THE INVENTION

The present invention relates to ultrasonic detection and measurement systems utilized to detect internal structural flaws within an object or material, for example, in such crucial structures as airline wings, by transmitting ultrasonic pulses to a target object and analyzing echo signals detected from the target object. The system and method of the invention also relate generally to systems utilized for applications such as corrosion measurements, thickness measurements and the like. More particularly, the present invention relates to a time variable gain (TVG) amplifier adopted for such systems.

The prior art of ultrasonic flaw detectors is exemplified by such products as the instant assignee's Epoch 4 Plus product. Competitive products available from General Electric are known as the USM 35X, USN 58L and USN 60 fault detection systems. In general, prior art ultrasonic flaw detectors utilize highly complex analog front ends that contain many parts which pose especially difficult problems in terms of calibration, reliability, set up time, consistency of results and optimization for specific usages and settings.

Typical prior art ultrasonic flaw detectors include a transducer which is placed against the object to be tested and which works in conjunction with numerous analog circuits such as gain calibrators, preamplifiers and attenuators, variable gain amplifiers, and high pass and low pass analog filters that operate over many different frequency bands and which need to be carefully calibrated and maintained.

As a result, present flaw detectors present a host of problems to designers and users of such equipment, which impact their troubleshooting and repair owing to their complexity. These problems include such issues as matching input impedances seen by the transducer which changes with different gain amplifiers that are switched in and out of the signal path. This adversely impacts the frequency response and introduces various gain nonlinearities. It poses issues of calibration, as analog circuits are switched in and out of the signal path.

Another problem with existing flaw detectors is attributable to their backwall attenuation performance which impacts the ability to detect flaws that are located very near the back wall of the object being tested. This problem poses particular problems with the time varied gain function which has a limited gain range and gain rate of change in prior art devices.

Another prior art drawback ensues from the manner in which analog circuits are coupled, which results in each amplifier in the signal path having different DC offset errors that must be nulled in order to keep the input signal at the mid-point of the analog to digital converter being utilized, in order to present a signal level to the converter which matches the full amplitude scale of such converter. The error nulling processes in the prior art are therefore unreliable, particularly at high gain, due to DC baseline measurement inaccuracies caused by noise.

The intensely analog implementation of the front ends of existing flaw detectors poses further issues owing to the need to utilize the entire dynamic range of the instrument that is being utilized which creates various gain linearity calibration issues.

An ultrasonic inspection apparatus of the prior art is described in U.S. Pat. No. 5,671,154, which provides background information for the apparatus and method of the present invention. A tunable digital filler arrangement is described in U.S. Pat. No. 6,141,672.

SUMMARY OF THE INVENTION

Generally, it is an object of the present invention to provide an apparatus and method for ultrasonic inspection and measurement of objects which avoid or ameliorate at least some of the aforementioned drawbacks of the prior art.

It is a further object of the invention to provide an ultrasonic inspection apparatus and method that is implemented in simpler circuitry.

It is a further object of the present invention to provide an ultrasonic inspection apparatus and method that requires a shorter and simpler process of calibration and adjustment prior to use.

The foregoing and other objects of the invention are realized in an apparatus and system which includes a transmit and receive device to generate a test signal and to receive a responsive echo signal and a transducer which converts the test signal to an ultrasonic signal and produces the echo signal for the transmit and receive device. A signal processing circuit processes the echo signal and stores streaming information defining the echo signal in a digital memory. A logarithmic TVG (time variable gain) device processes the information by applying a time varying gain function to it and the resulting data is presented to one or more filters being ultimately output to a user. The logarithmic TVG device specifies the gain slope between various signal amplitude ranges to process it in a simpler algorithm.

Other features and advantages of the present invention will become apparent from the following description of the invention which refers to the accompanying drawings.

BRIEF DESCRIPTION OF THE DRAWINGS

FIG. 9 is a block diagram of the logarithmic TVG of FIG. 8a.

FIGS. 12, 13, 14, 15 and 16 are block diagrams illustrating, respectively, second, third, fourth, fifth and sixth embodiments of the TVG of FIG. 8a.

DETAILED DESCRIPTION OF PREFERRED EMBODIMENTS OF THE INVENTION

Figure 1:
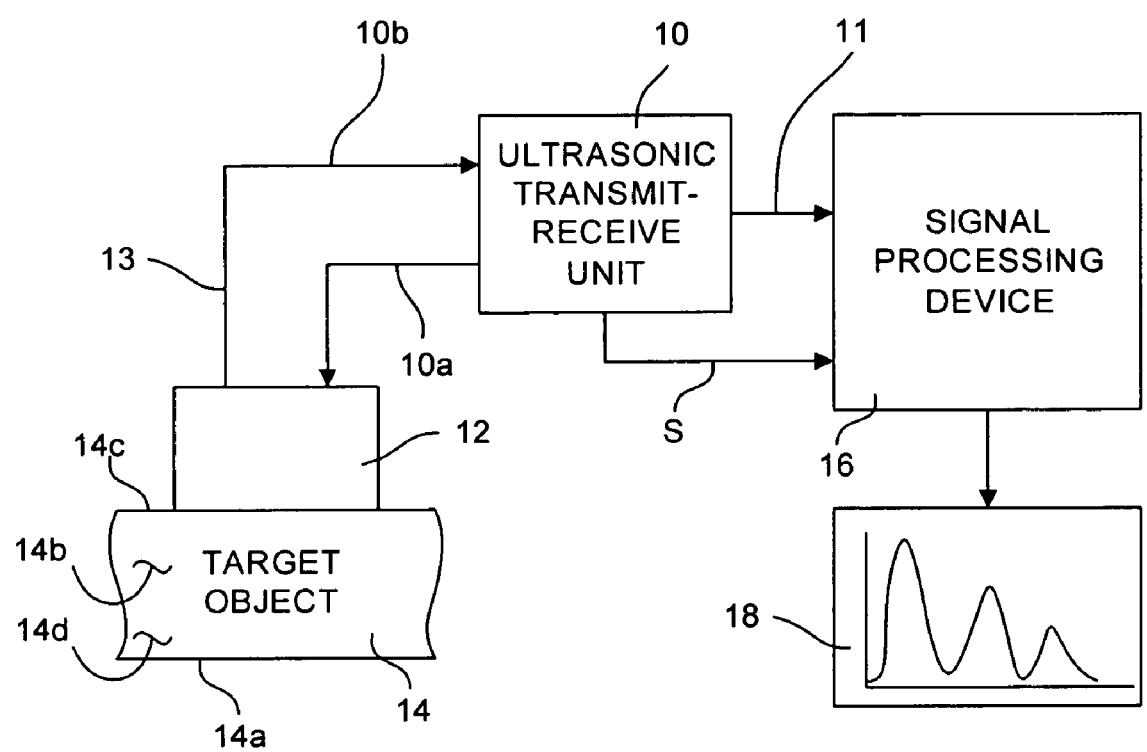
FIG. 1 is block diagram of a basic arrangement of an ultrasonic inspection apparatus.
Figure 2:
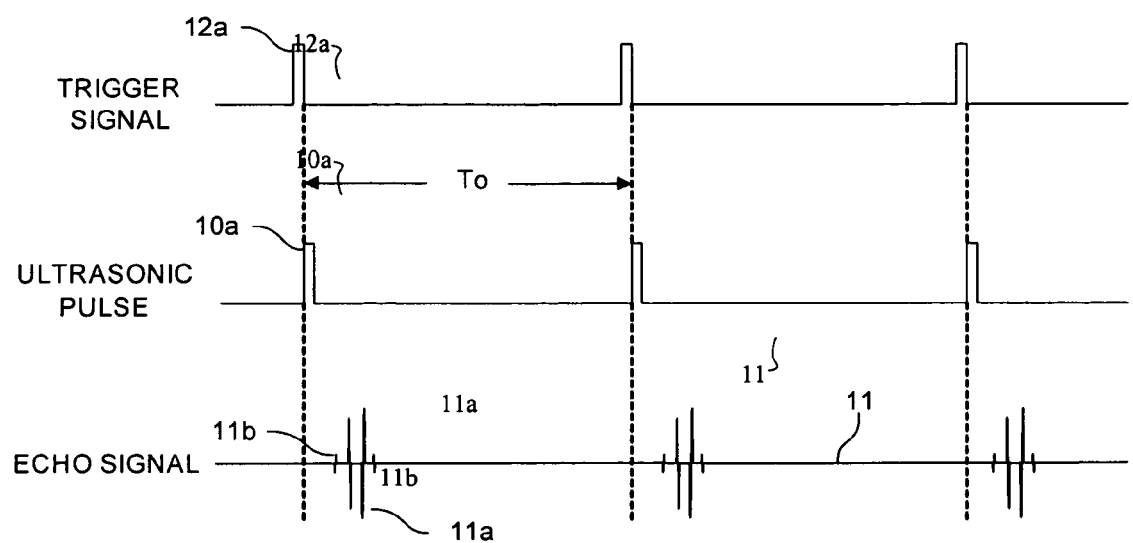
FIG. 2 is a basic waveform diagram for the device of FIG. 1.

Reference is initially made to FIGS. 1 and 2, to provide background information on the general environment of and various problems solved by the present invention.

In FIG. 1, an ultrasonic transmit-receive unit 10 transmits an electrical pulse signal 10a at a predetermined period to a probe or transducer 12 which is coupled to a target object 14, such as to steel material, directly or through a delay material such as water or quartz. As shown in FIG. 2, the probe 12 converts the trigger pulse signal 12a into an ultrasonic pulse 10a which it transmits through the target object 14. The ultrasonic pulse 10a applied into the target object 14 is subsequently reflected by a bottom surface 14a of the target object 14 and received by the probe 12. The probe 12 converts the reflected wave into an electrical signal which is supplied as an electrical echo signal 10b to the ultrasonic transmit-receive unit 10. The ultrasonic transmit-receive unit 10 amplifies the electrical signal 10b and transmits the amplified signal 11 to a signal processing device 16 as an echo signal 11.

The echo signal 11 includes a bottom surface echo 11a corresponding to the wave reflected by the bottom surface 14a and a flaw echo 11b caused by a flaw 14b in the object 14. In addition, the frequency of the ultrasonic echo pulse 11 is determined primarily by the thickness or other property of the ultrasonic vibrator incorporated in the probe 12. The frequency of the ultrasonic pulse 10a used for inspection is set to tens of kHz to tens of MHz. Therefore, the frequency range of the signal waveforms of the bottom surface echo 11a, and the flaw echo 11b included in the echo signal 11 cover a wide range of from about 50 KHz to tens of MHz.

The signal processing device 16 performs various signal processing of the echo signal 11 received from the ultrasonic transmit-receive unit 10, and the signal processing device 16 displays on a display unit 18, an output result that represents the presence/absence of a flaw or flaws. In order to signal process the echo signal 11 and display the echo signal, a trigger signal S synchronized with the pulse signal 10a is supplied from the ultrasonic transmit-receive unit 10 to the signal processing device 16.

In the flaw inspection apparatus arranged as described above, the echo signal 11 output from the ultrasonic transmit-receive unit 10 includes, in addition to the bottom surface echo 11a and flaw echo 11b, a certain amount of noise. When the amount of noise included in the ultrasonic pulse 11 is large, the reliability of an inspection result is considerably degraded. The noise is roughly classified into electrical noise and material noise.

The electrical noise comprises external noise caused by mixing an electromagnetic wave into the probe 12, the ultrasonic transmit-receive unit 10, connection cables, e.g., cables 13, or the like, and internal noise generated by amplifier(s) and the like incorporated in the ultrasonic transmit-receive unit 10.

Reduction of the noise included in the echo signal 10b is very important to perform ultrasonic inspection at high accuracy. Conventionally, an analog filter is used to reduce noise components included in the echo signal 10b. For example, a BPF (Band pass Filter) is used to pass the frequency component of the ultrasonic echo relative to the electrical noise having a wide-frequency component. In addition, an LPF (Low-Pass Filter) or a BPF is used for material noise, recognizing that the frequency distribution of the flaw echo 11b (FIG. 2) is lower than that of the echo produced by signal scattering. In this manner, when an analog filter is used, noise components included in the echo signal 11b can be reduced to a level equal to or lower than a predetermined level.

It is generally known that the frequency distribution of a flaw echo signal changes based on the ultrasonic attenuation characteristics of the target object 14. Therefore, when a BPF is to be used for material noise represented by a scattered echo or the like, a filter having optimal characteristics is desirably used in accordance with the target object 14. However, since the passing frequency characteristic of the analog filter cannot be easily changed, a larger number of filters, having different passing frequency characteristics corresponding to the different ultrasonic attenuation characteristics of the various materials associated with target objects 14 must be prepared. In this manner, when different filters are used in accordance with the material characteristics of target object 14, practical difficulties occur in consideration of operability or economic advantages versus the cost and complexity of the overall system.

Figure 3:
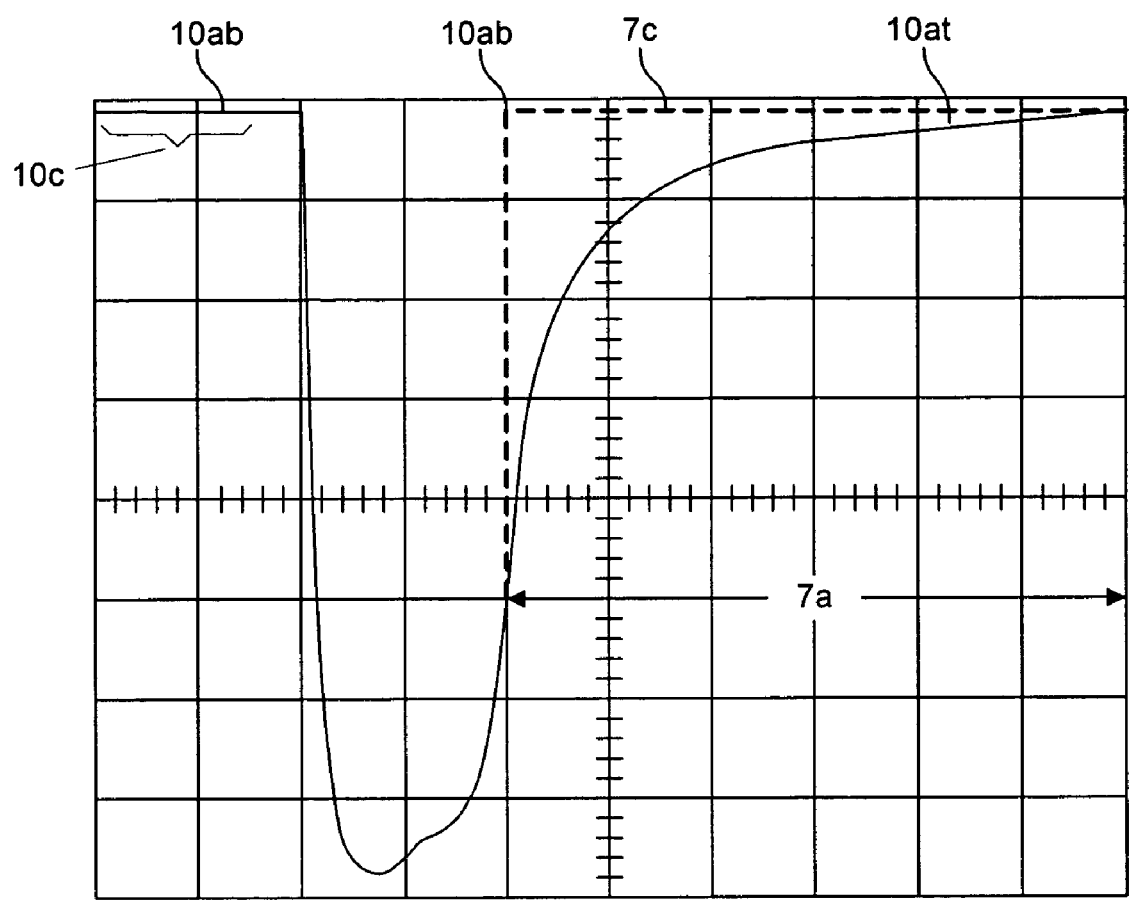
FIG. 3 is a waveform diagram illustrating the trailing edge characteristic of an ultrasonic pulse.

In some cases, the flaw echo 11b may be very close to the front surface 14c of target object 14 which will place it in close proximity to the trailing edge of transmitted pulse 10a. For this reason, it is desirable for the end of the trailing edge (magnified as trailing edge 10at in FIG. 3) of the transmitted pulse 10a to settle to the zero base line 10ab as quickly as possible in order not to interfere with the returning flaw echo 11b. The settling time to the zero base line 7a is a determining factor of a flaw detector's near surface resolution.

Considering that the gain of the ultrasonic transmit-receive unit 10 can be adjusted up to 110 dB (as required by European standard EN 12668-1), a small amount of base line error prior to a gain amplification stage in the ultrasonic transmit-receive unit 10 will cause a large error at the output of the gain amplification stage if the gain level is set too high.

The resulting base line error at the input to the signal processing device 16 will either:

(a) cause the dynamic range to be reduced because the maximum vertical displacement of the signal on the screen will be reduced by the amount of offset of the base line, which produces a reduction in the instrument's sensitivity to detecting flaw echoes, or (b) if sufficiently high in amplitude, cause a gain amplification stage, or gain amplification stages, to saturate, thereby preventing an echo signal from being detected at all.

Conventionally, the base line error problem described above is addressed in one of two ways. In accordance with a first approach, a HPF is used in the signal path of the input of ultrasonic transmit-receive unit 10 in order to filter out the low frequency content of the trailing edge 10at of the transmitted pulse 10a. The trailing edge 10at of the transmitted pulse 10a can be improved by the HPF as is indicated by the approximated dotted line 7c.

However, the effectiveness of the HPF solution is limited in several manners. First, the HPF cutoff frequency (f HPF −3 dB) must be as high as possible to minimize the low frequency content of the trailing edge 10at of the transmitted pulse 10a. For example, if the excitation frequency of probe 12 is 10 MHz and the f HPF −3 dB is 5 MHz, the undesirable effect on the receiver base line is greatly reduced.

Unfortunately, it is not uncommon to use an excitation frequency for probe 12 as low as 500 kHz which would require the f HPF −3 dB to be below 500 kHz. The HPF solution loses much of its effectiveness in this frequency range because an undesirable amount of the low frequency content of the trailing edge 10at of the transmitted pulse 10a is allowed to pass through the HPF and contribute to base line error.

Secondly, the maximum amplitude of the transmitted pulse applied to a first amplifier stage (not shown) of ultrasonic transmit-receive unit 10 is limited (clamped) to a few volts in order to prevent damage to the amplifier circuit. It is common to operate the gain of the ultrasonic transmit-receive unit 10 at a level that will cause the amplifiers to saturate every time the pulser is fired. If the filters are not critically damped, the filter response after coming out of saturation will cause the trailing edge of the transmitted pulse 10a to be worse than if no filtering was applied. It is possible for each manufactured instrument to have the numerous filters tuned to ensure critical damping; however, practical difficulties occur in consideration of manufacturability and long term temperature drift of the filter components.

It should also be noted that once an amplifier goes into saturation, it takes a significant amount of time for the amplifier to return to the linear region of operation. This causes the trailing edge of the transmitted pulse 10a to take more time to return to the zero base line than would be the case if the amplifier input signal remained below the saturation level (i.e. within the linear range of operation).

An alternate method used to address the base line error problem is to directly couple the clamped transmitted pulse 10a to the input of ultrasonic transmit-receive unit 10. This method avoids one of the problems described above, because no HPF or BPF filters are used.

The effectiveness of the direct coupling solution is limited in two ways. First, it does nothing to reduce the low frequency content of the trailing edge 10at of the transmitted pulse 10a. Secondly, the DC component of the base line error and the offset errors of the amplifiers of the ultrasonic transmit-receive unit 10 pass through the signal path and are amplified. This can cause various dynamic range and saturation problems described further on.

Conventionally, flaw detectors have provisions that allow the user to operate the instrument either with filters or through direct coupling in order to select the optimal setting for the flaw measurement scenario.

Figure 4:
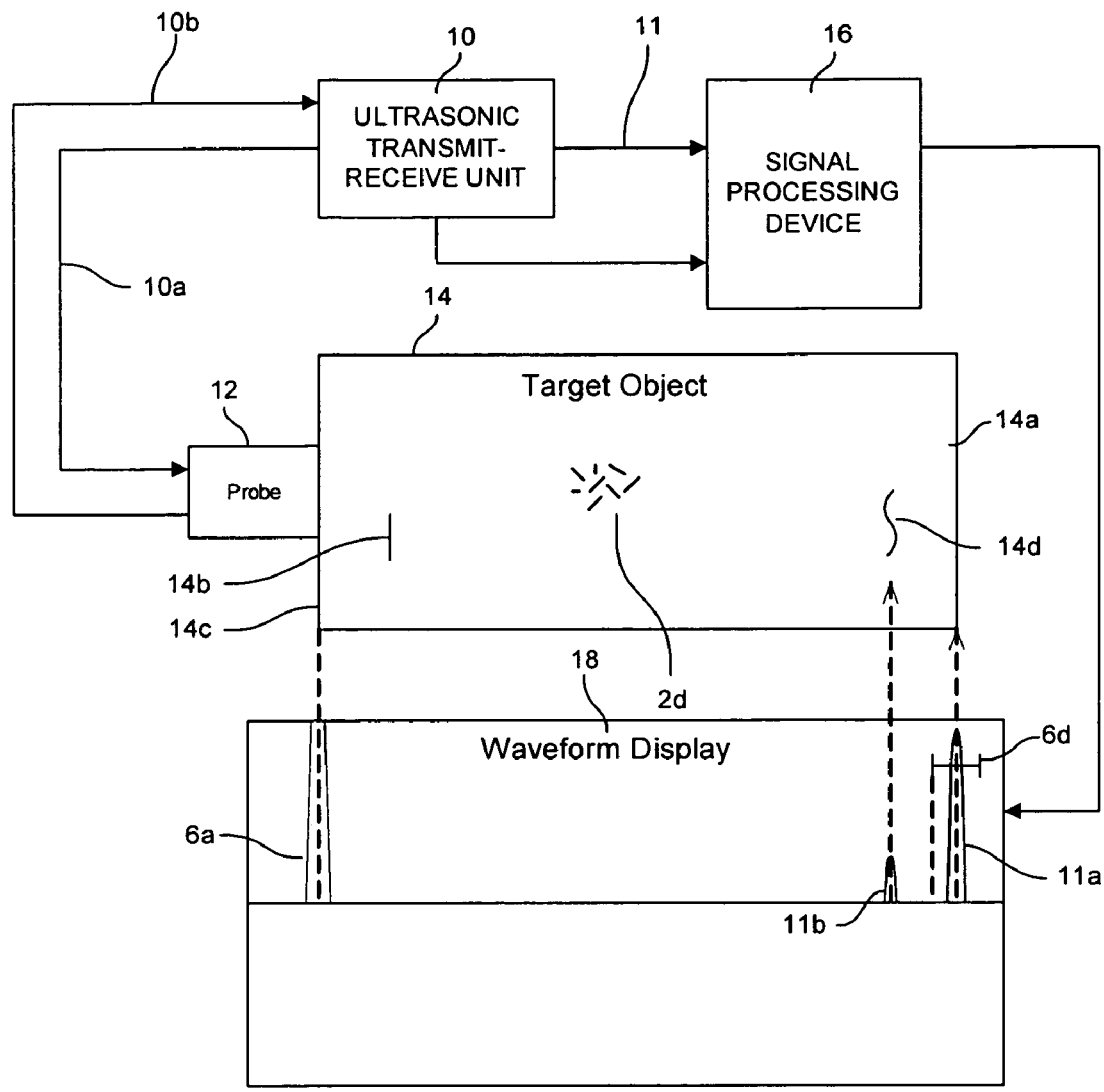
FIG. 4 is a block diagram that provides a side-by-side comparison of a waveform display with fault locations in a target object.

Reference is now made to FIG. 4 to describe detection of flaws near the rear surface of the object 14. In some cases, a flaw 14d may be very close to far surface 14a of target object 14 which will place the flaw echo 11b in close proximity to back wall echo 11a. In order to perform a proper inspection (in accordance with many formal inspection procedures), the peak of back wall echo 11a must remain visible on the waveform display 18 at all times. The reasons for this are: 1) small flaws in target object 14 caused by porosity or material contaminants may generate flaw echoes that are not large enough to be seen on the waveform display 18, but may reduce the amplitude of the echo traveling to back wall 14a, thereby causing the amplitude of flaw echo 14d and back wall echo 11a to be reduced, and 2) probe 12 may be improperly coupled to the surface 14c of target object 14 intermittently, thereby reducing the amplitude of back wall echo 11a. These two conditions may cause the echo of flaw 14d to not be visible on the waveform display 18. However, the reduction in back wall echo 11a will indicate a problem with the target object 14 material or the coupling of probe 12. If the peak of back wall echo 11a was allowed to go beyond the top visible portion of the waveform display 18, a reduction in peak amplitude may not be visible on waveform display 18. The person performing the inspection sets up the back wall echo 11a detection parameters by adjusting back wall echo gate 6d (see FIG. 4) to set the region on the horizontal time axis where the back wall echo 11a is permissible. A threshold on the vertical amplitude axis is also set for the minimum acceptable echo amplitude. Typically, an alarm will occur when back wall echo 11a falls out of these parameters.

This measurement method produces certain problems.

The difference in echo amplitude between the flaw echo 11b and back wall echo 11a can be huge (as much as several orders of magnitude). But several methods described below (a, b, c and d) can be used to ensure that flaw echo 11b and the peak of back wall echo 11a both remain visible on waveform display 18. (Note that although these methods have limitations as compared to the present invention, there are many applications for which they can provide satisfactory performance.)

(a) Connect probe 12 to two parallel receiver and A/D converter channels (A and B). The gain of channel A is adjusted by the person performing the inspection to optimize the amplitude of the echo of flaw 14d to make it is clearly visible on waveform display 18. The gain of channel B is adjusted to ensure that the peak of the back wall echo 11a remains visible on waveform display 18 for the reason previously described.

The digital outputs of the channels A and B A/D converters are combined in such a way that the entire horizontal time scale of waveform display 18 shows all of the output of the channel A except for the region of back wall echo gate 6d. The leftmost side of back wall echo gate 6d indicates the point in time when the switch over from channel A to channel B would occur.

Unfortunately, the two channel method has disadvantages. Typically, an inspection is performed by moving probe 12 along the surface of target object 14 in a scanning motion because the presence or location of a flaw inside of the target object is not known until it is detected. If the target object does not have a constant thickness between front surface 14c and back surface 14a in the scanning area, the back wall echo gate 6d will need to be adjusted wide enough to include this variation in thickness in order not to miss the detection of back wall echo 11a.

The near the backwall detection problem can be solved if both channels are stored and the channel change is carried out in the post processing. This would be a "tracking backwall attenuator" solution. Also a dual or split display window could be used, one to show flaws the other the backwall. This would remove the need to track the backwall and adjust the display. A small section of the received signal would be displayed twice—once at high gain in the flaw section and then again at low gain in the back wall section. This method can only support a flaw alarm gate that detects flaws that are very close to the back wall if the gate position is calculated in the post processing.

Consequently, back wall flaw echo 11b will not be detected if it is very close to back surface 14a because back wall flaw echo 11b will occur within the region of back wall echo gate 6d. This causes an undesirable effect on near surface resolution by far surface 14a. Further, the amount of receiver hardware is approximately twice as much as is required for a single channel solution.

(b) The two successive pulse-receive measurement cycles method is similar in concept to the two parallel receiver and A/D converter channels method except only one channel is required. The description in section (a) above applies to the two successive pulse-receive measurement cycles method. Also, instead of processing the flaw echo 11b and back wall echo 11a in two parallel channels set to different gains, the echoes are processed in the same channel, one pulse-receive cycle after the other, but with a different gain for each cycle.

A disadvantage that is unique to the successive pulse-receive measurement cycles method is that flaw echo 11b is separated in time from back wall echo 11a by an additional pulse interval To (shown in FIG. 2). Therefore, measurement errors are more likely to occur when probe 12 is moved in a scanning motion because its location will change between the time that flaw echo 11b and back wall echo 11a are measured.

(c) Time varied gain (TVG) is a single channel solution wherein the gain of the amplifiers of the ultrasonic transmit-receive unit 10 is dynamically changed to optimize the amplitude of flaw echo 11b and back wall echo 11a (for the reason already described).

The TVG method has the same disadvantage for near surface resolution by far surface 14a as the two parallel receiver and A/D converter channels method does.

Figure 5:
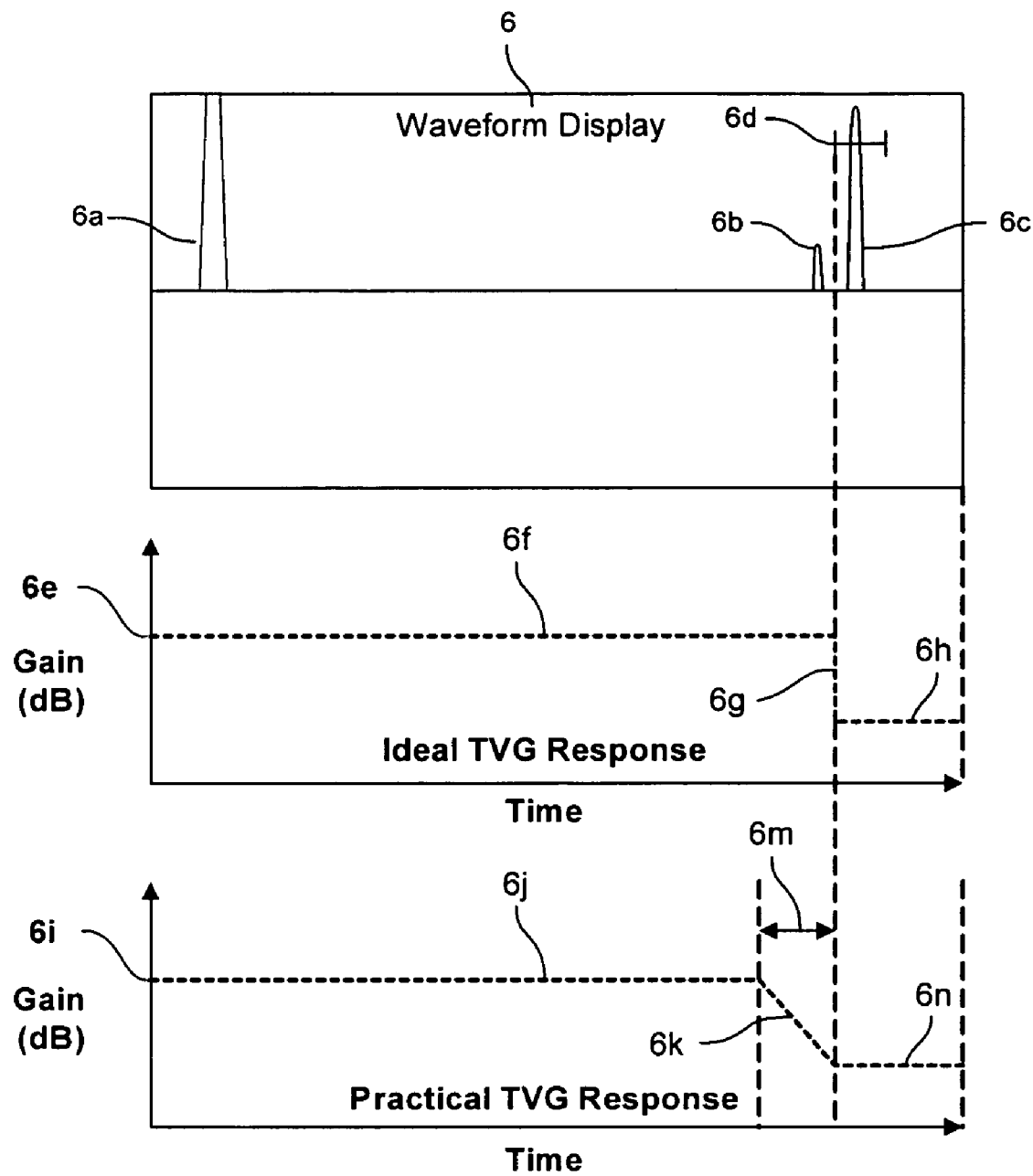
FIG. 5 is a continuation of FIG. 4.

There are other disadvantages associated with the TVG method. Thus, FIG. 5 shows an ideal TVG curve 6e that changes instantaneously from gain 6f to gain 6h, thereby introducing no additional near surface resolution error from the analog TVG amplifier. The error described in method a above would still remain.

Unfortunately, it is impossible for analog TVG amplifiers to achieve the ideal curve 6e (especially, the instantaneous slope 6g). Analog TVG amplifiers and the external signals that control them have response times that limit gain rate of change 6g, thereby causing an undesirable effect on the near surface resolution by far surface 14a. The near surface resolution degrades because flaw 14d must be farther away from rear surface 14d of target object 14 in order to provide time interval 6m for the gain to change. Stated in terms of the echoes of interest, flaw echo 11b must occur before the start of time interval 6m, and back wall echo 11a must not occur before the end of time interval 6m.

The other problem associated with the TVG method is caused by the various sources of DC offset errors in the receiver section of ultrasonic transmit-receive unit 10. The sources include the input DC offset errors of the amplifier IC's and the DC component of the base line error.

The DC offset errors present in certain existing flaw detectors of the present assignee are compensated for at each gain setting every time the gain is adjusted from one level to the next. The DC offset errors are compensated for in this way to take into account the effects of temperature, and long term stability, drift on the DC offset errors, etc. The compensation method uses several D/A converters along the receiver signal path to inject a DC null signal that will ensure that the base line remains on the center of the A/D converter's full scale range and in an optimal location on waveform display 18. Every time the instrument is turned on, or the gain setting is changed, an algorithm runs in a microprocessor that takes a base line error reading, calculates the DC error correction value required, and sets the DACs to this value.

It is not practical to perform the DC offset compensation method described above for every gain setting at the speed that the TVG is required to operate at. Instead, the DC offset correction is set for the midpoint gain, thereby splitting the error between the end points. For example, if the TVG range is set to operate between 20 and 60 dB, the DC offset correction is set to compensate for the error at 40 dB. The problem with this technique is that it introduces errors to echo amplitudes that are undesirable for an accurate flaw detection and sizing.

(d) Logarithmic amplifiers are used to cover the huge dynamic range required and the echoes are shown on the waveform display 18 on a logarithmic scale. The logarithmic scale provides a very high dynamic range thereby allowing both a low amplitude flaw echo and the peak of the much higher amplitude back wall echo to be visible on a waveform display.

Unfortunately, certain undesirable consequences occur when using the logarithmic method. Thus, for a given back wall echo amplitude and amplitude variation, the vertical variation of the peak of the echo waveform is much less noticeable on the waveform display than for a receiver that uses linear amplifiers. This would make it more difficult to detect a flaw by observing the peak amplitude variation of the back wall echo, as described earlier.

Further, the output of the logarithmic amplifier provides a rectified waveform. Therefore, the location of the negative echo lobe cannot be identified because it is either removed by half-wave rectification, or converted into a positive lobe by full wave rectification. The precise location of both the positive and negative echo lobes is very important for measuring the thickness of target object 14 accurately because one lobe may be more visible than the other. The polarity of the echo lobes is also required to determine when echo phase inversion occurs. Phase inversion of an ultrasonic echo occurs when a sound wave passes from a material of low acoustic impedance to a material of high acoustic impedance.

Furthermore, all filters must be located prior to the logarithmic amplifier section because the filters require linear signals to operate correctly (a logarithmic amplifier is a non-linear device). The receiver will have a much higher susceptibility to noise if the filter circuits are located prior to the high gain logarithmic amplifier section because the PCB traces required to connect the filter components together are susceptible to electromagnetic noise, and the internal noise generated by an filter amplifiers will be maximally amplified.

Figure 6:
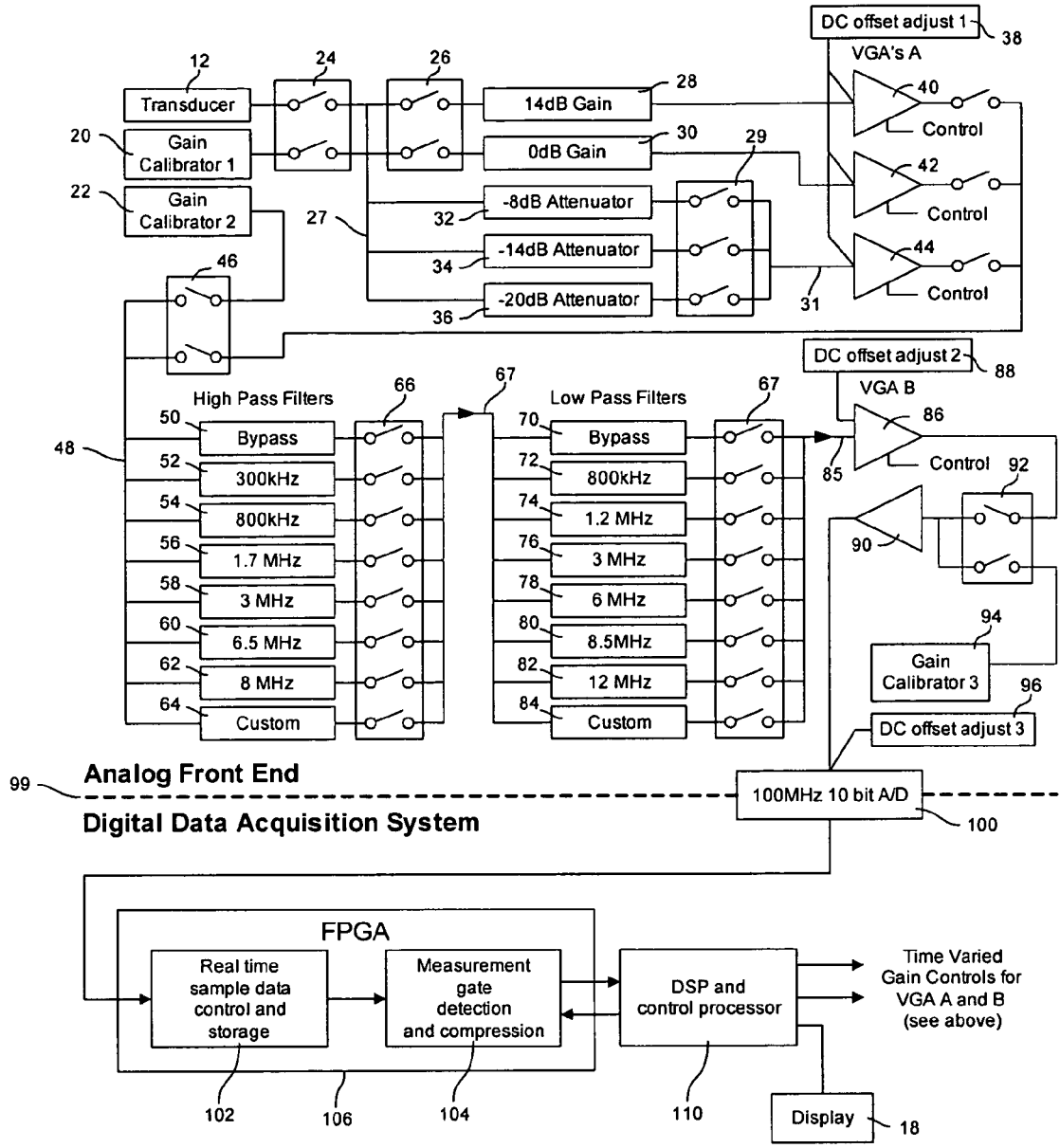
FIG. 6 illustrates a circuit block diagram of a prior art implementation of an ultrasonic inspection apparatus.

A more detailed version of a prior art circuit which has been utilized to implement an ultrasonic inspection system is illustrated in block diagram form in FIG. 6. This intensely analog circuit utilizes the signal from the transducer 12 to feed it through a switch 24 as one selectable input to a series of parallelly provided amplifiers and/or attenuators 28, 30, 32, 34 and 36, which have respective gains of 14 dB, 0 dB, -8 dB, -14 dB and -20 dB, respectively. The switch 24 also receives the input of a gain calibrator 20 and provides its signal directly to attenuators 32, 34 and 36, and via switch 26 to the amplifiers 28 and 30.

Variable gain amplifiers (VGA) 40, 42 and 44 respectively receive their inputs from the amplifiers 28 and 30 and from the switch 29, which provides an output 31 that constitutes the selected one of the outputs of attenuators 32, 34 and 36. The outputs of the VGAs are provided to a switch 46 which also receives as one of its inputs, a signal from gain calibrator 22 and selectively providing these signals over a bus line 48 to a series of high pass filters 50, 52, 54, 56, 58, 60, 62 and 64, whose outputs are switched through a switching network 66 to low pass filters 70, 72, 74, 76, 78, 80, 82 and 84. Thus, the signals from the VGAs 40, 42 and 44 or from the gain calibrator 22 can be fed by controlling the selection of a desired signal through the switches 66 and 67 to provide it to a further, downstream VGA 86, whose output is further provided through a switch 92 to an amplifier 90.

The output of this amplifier 90 or the output of a gain calibrator 94 are then finally fed to the 100 MS/s 10 bit analog to digital (A/D) converter 100.

A field programmable gate array (FPGA) 106 incorporates a real time sample data control and storage circuit 102, and a measurement gain detection and compression circuit 104 to provide an output to the digital signal processor and control 110, which also controls the settings of the FPGA 106 to obtain the appropriately processed interpolated output of the analog to digital converter 100, providing time varied gain control, and for producing a signal that can be displayed on the display 18.

In view of the introductory discussion, it is readily apparent that the tasks of calibrating the various analog circuits to prevent inconsistencies and variations attributable to different frequency responses of the numerous high pass and low pass filters, and avoiding the DC offsets and drifts and temperature effects of the analog devices present enormous challenges to both designers and users of the prior art circuits.

Figure 7:
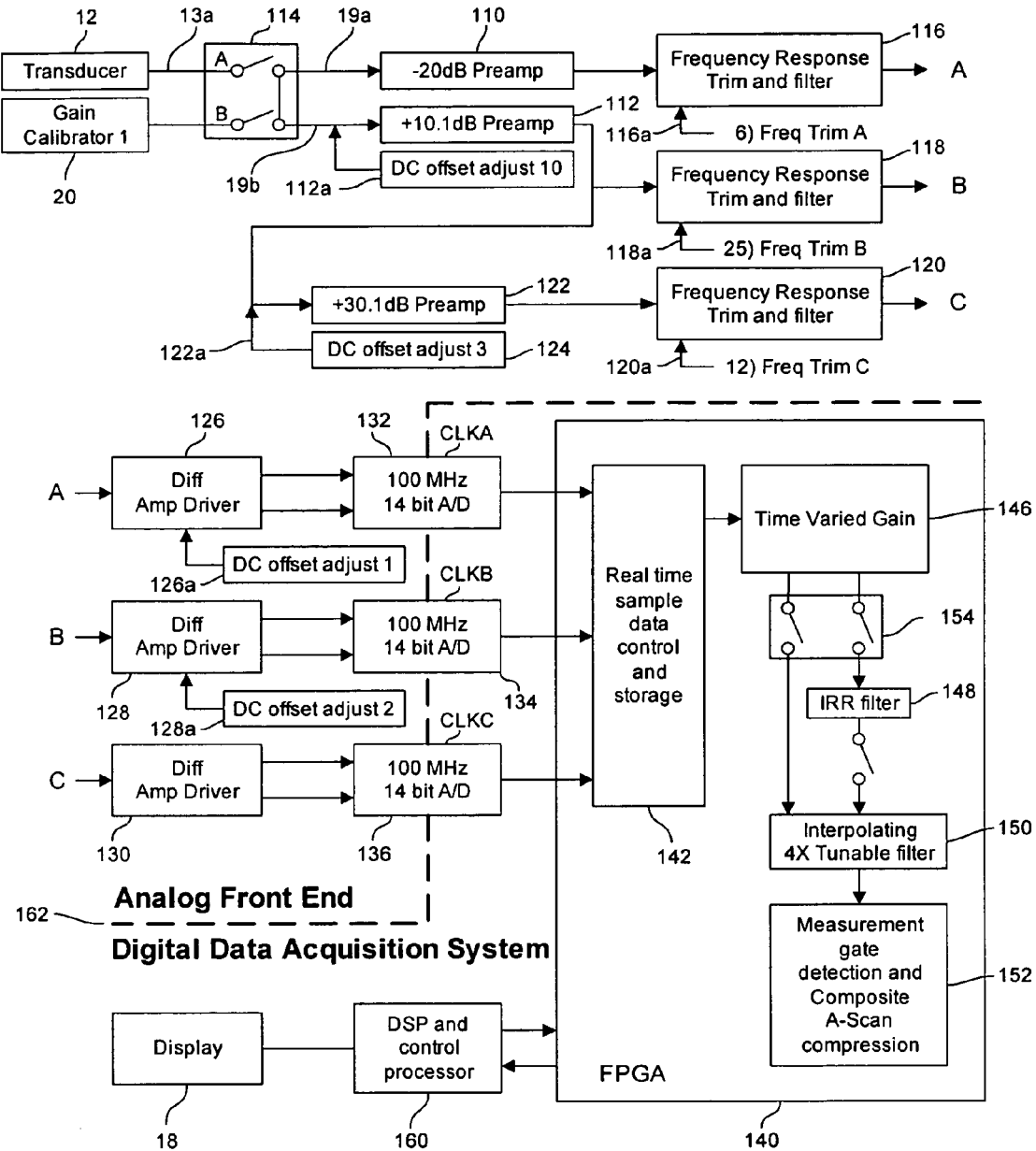
FIG. 7 is a circuit diagram of a digitally intensive implementation of an ultrasonic inspection apparatus in accordance with the present invention.

A cursory comparison of the block diagram of the present invention presented in FIG. 7 illustrates the far scarcer usage of the problem prone analog circuits in the instant invention, which utilize triple A/D channels that avoid many of the drawbacks and complexities of the prior art.

In the block diagram of FIG. 7, when switch 114a is closed, the transducer 12 has its output 13a provided directly to only two preamplifiers 110 and 112, the latter amplifier feeding a third amplifier 122. The signals of these amplifiers are processed, respectively, in frequency response trim and filter blocks 116, 118 and 120 and subsequently provided along the three channels A, B, C to differential amplifier drivers 126, 128 and 130. The analog signals along the three channels are then provided directly to A/D converters 132, 134 and 136, respectively, whose digital outputs in turn are then supplied to the field programmable gate array 140, which incorporates a control and storage block 142, a digital logarithmic integrator time varied gain 146, and a measurement gate detection and composite A-scan compression circuit 152. This FPGA 140 works in conjunction with the DSP 160, which provides its signal to the display 18.

The implementation in FIG. 7 dispenses with most of the analog circuits and the drawbacks of the prior art, including the intensive use of analog high pass and low pass filters, additional amplifiers and calibrators, and various VGA circuits, all of which are rendered unnecessary in accordance with the circuits of FIG. 7.

Figure 8:
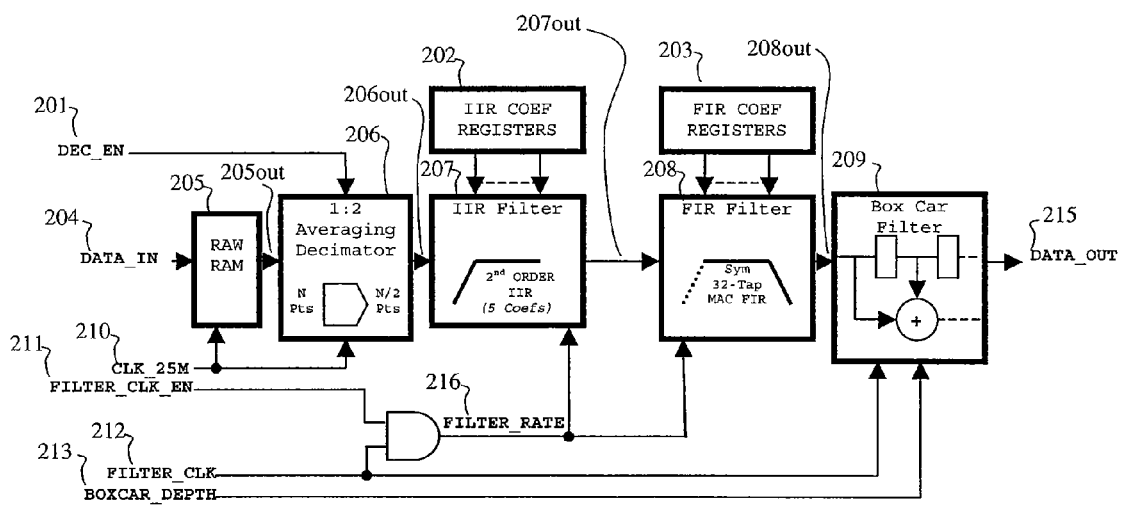
FIG. 8 illustrates a tunable digital filter which is usable with the instant invention.

With reference to the field programmable gate array 140 of FIG. 7, attention is now directed to FIG. 8 which implements a portion thereof, including its real time sample data control and storage, filtering function and interpolating functions.

Preliminarily, it is noted that the block diagram of FIG. 8 effectively provides a tunable digital filter with adaptable sampling rates that are dependent on the pass band settings of the device. The device is intended for use in ultrasonic and eddy current industrial test instruments.

The interpolator part of the invention creates an effective sampling rate of 400 MS/s for frequencies below the Nyquist frequency (50 MHz) while using only 100 MS/s A/D converter sample data.

Existing Flaw Detector products, such as the instant assignee's Epoch 4 Series, have an interleave function that effectively increases the A/D converter sample clock resolution by performing two successive measurement cycles.

An undesirable effect due to interleaving occurs when the transducer probe and object being inspected are in motion relative to one another. To obtain an accurate measurement result during interleaving, the ultrasonic measurement event must be repeatable. Therefore, the placement of the transducer probe with respect to the object being tested must be as unchanged as much as possible during the interleave period.

In a novel manner, the preferred approach of the present invention achieves a 4× increase of the sampling rate above the A/D converter sampling rate without the need for multiple measurement cycle interleaving, for the case of the specifically described embodiment described below.

With further reference to FIG. 8, the RAW RAM 205 basically corresponds to the element 142 in FIG. 7 and constitutes the device that stores the data from the analog to digital converters, such as the converters 132, 134, 136 of FIG. 7. The RAW RAM 205 is preferably a dual port RAM that can store and playback data, at data rates of 100 MS/s. Operating at clock rate of, for example, 25 MS/s, data read from RAW RAM 205 is fed to averaging decimator 206, which receives an enable signal 201 and provides information to an UIR (Infinite Impulse Response) filter 207 which filters the data based on a filtering function defined by operator settable values stored in IIR coefficient registers 202. This infinite impulse response type filter operates at a rate which is determined by a filter clock 212 which is enabled by a filter clock enable 211 and provides the gated filter clock 216 to the IIR filter 207, as shown.

A finite impulse response (FIR) filter 208 provides a further filtering function that is shaped and defined by data stored in FIR coefficient registers 203. The FIR filter 208 operates synchronously with the IIR filter 207. A box car filter 209 receives the data from the FIR filter 208 and provides its data output in the form of data 215. The box car filter 209 operates at the rate of the filter clock 212 and is further controlled by a box car depth signal 213 as shown.

Thus, the circuit of FIG. 8 effectively realizes digital data filtering while providing optimal filter response and while requiring minimal digital hardware in the form of logic gates, gate arrays, and the like. The minimization of the digital hardware reduces the size and cost required for the FPGA (field programmable gate array), and provides power consumption reductions. Low power consumption is important for achieving a longer battery life in portable instruments. Further, the invention also reduces part count considerably as compared to the analog filter implementation.

The present invention provides significant improvements to the conventional method of achieving time variable gain (TVG) in ultrasonic flaw detectors that use variable gain analog amplifiers (VGA's) controlled by a pre-loaded table of gain values spaced one 'time unit' apart.

Figure 10:
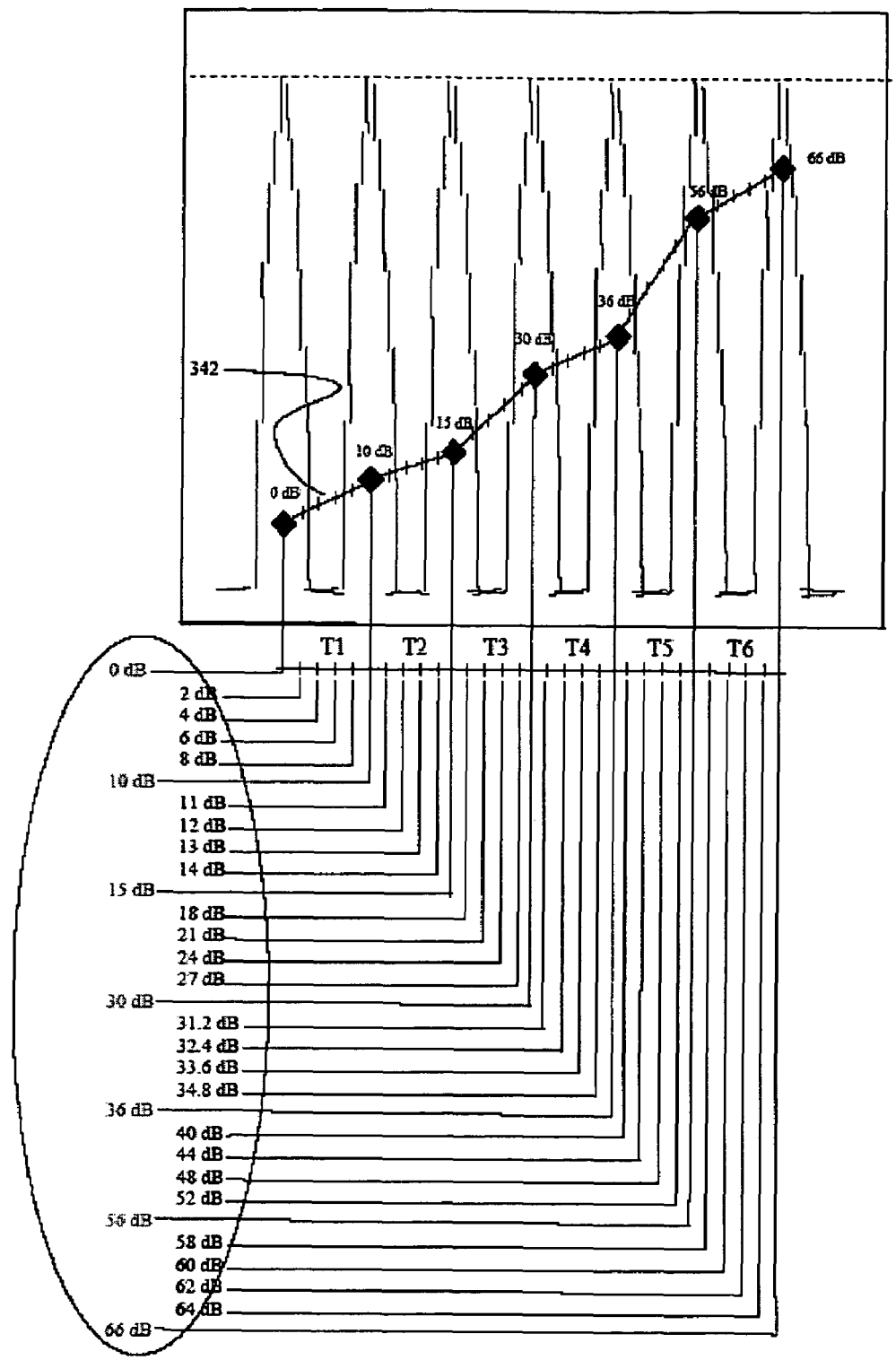
FIG. 10 is a diagram illustrating a prior art implementation of a TVG.
Figure 11:
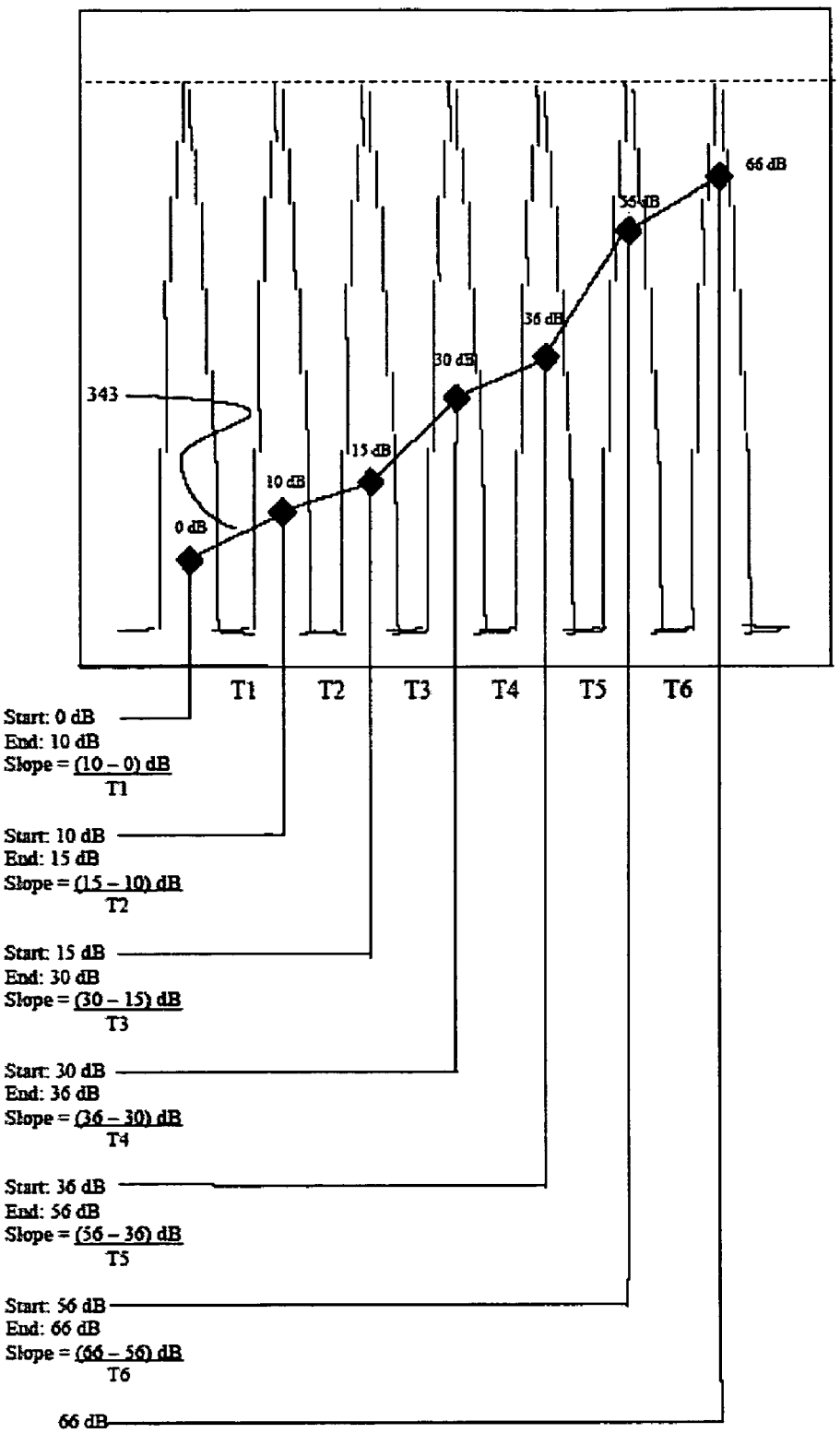
FIG. 11 is a diagram illustrating the TVG algorithm of the present invention.

Simplified illustrations of the conventional and new invention method are shown in FIGS. 10 and 11, respectively. In both cases, the TVG curve 342 and 343 respectively is created by establishing a starting gain value, end gain value, and the total time interval between the values. Therefore, for the first TVG line segment, 0 dB, 10 dB and T1 would be used respectively. This process is repeated for all TVG line segments from 10 dB to 66 dB.

The conventional TVG method and apparatus would require a digital memory device to store each gain setting across the entire TVG range of 0 dB to 66 dB. Therefore, for FIG. 10, thirty gain values would need to be stored and played back at a constant rate to the DAC controlling the VGA to produce TVG curve 342. Conventional implementations would actually use many more than thirty TVG points; however, only thirty points are used in FIG. 9 to simplify the diagram and explanation.

The present invention improves upon the conventional TVG method in the following ways:

a) The invention requires much less TVG digital memory for a given TVG curve because only the start gain value, end gain value and gain rate of change slope is required to generate the TVG curve line segments. Conventional list based TVG methods store the start gain value, end gain value, and every intermediate gain value of each TVG segment. Therefore, TVG curve 343 of FIG. 11 requires only eighteen memory locations instead of 30 as compared to FIG. 3. The reduction in memory size is much more significant than 30 to 18 because many more intermediate gain points are required to implement typical TVG functions when using the conventional TVG method.

b) The aforementioned problems associated with the analog components required to implement the conventional method are eliminated.

c) Much steeper TVG line segments can be realized because the invention method and apparatus are implemented completely digitally; therefore, the maximum time rate of change for gain can be as fast as the time interval between contiguous sample data which is 10 ns for a 100 MS/s A/D converter sampling system. This improvement will allow, by far, the best back wall attenuation performance in the industry.

Figure 8A:
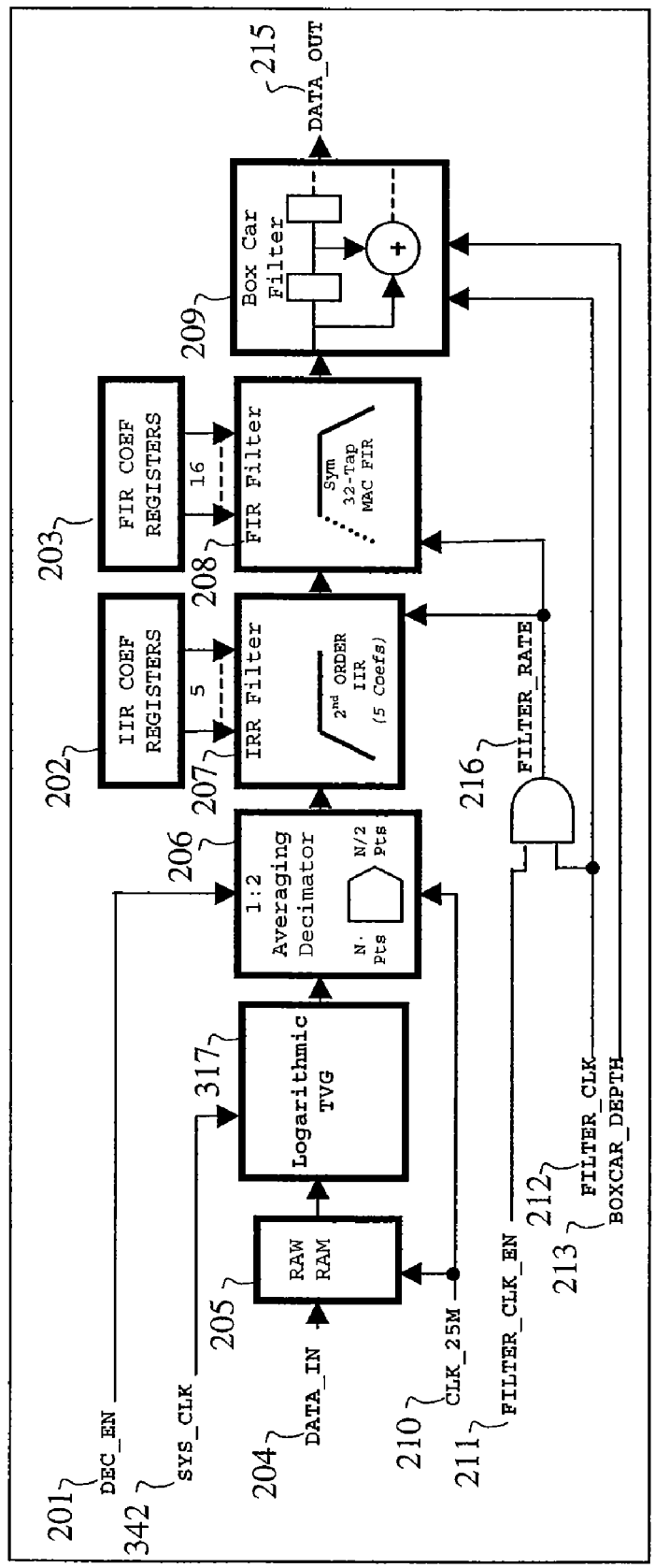
FIG. 8a incorporates a logarithmic TVG within the circuit of FIG. 8.

FIG. 8a shows the location of present logarithmic TVG 317 within the digital signal processing chain of a preferred embodiment shown in FIG. 8.

Figure 9:
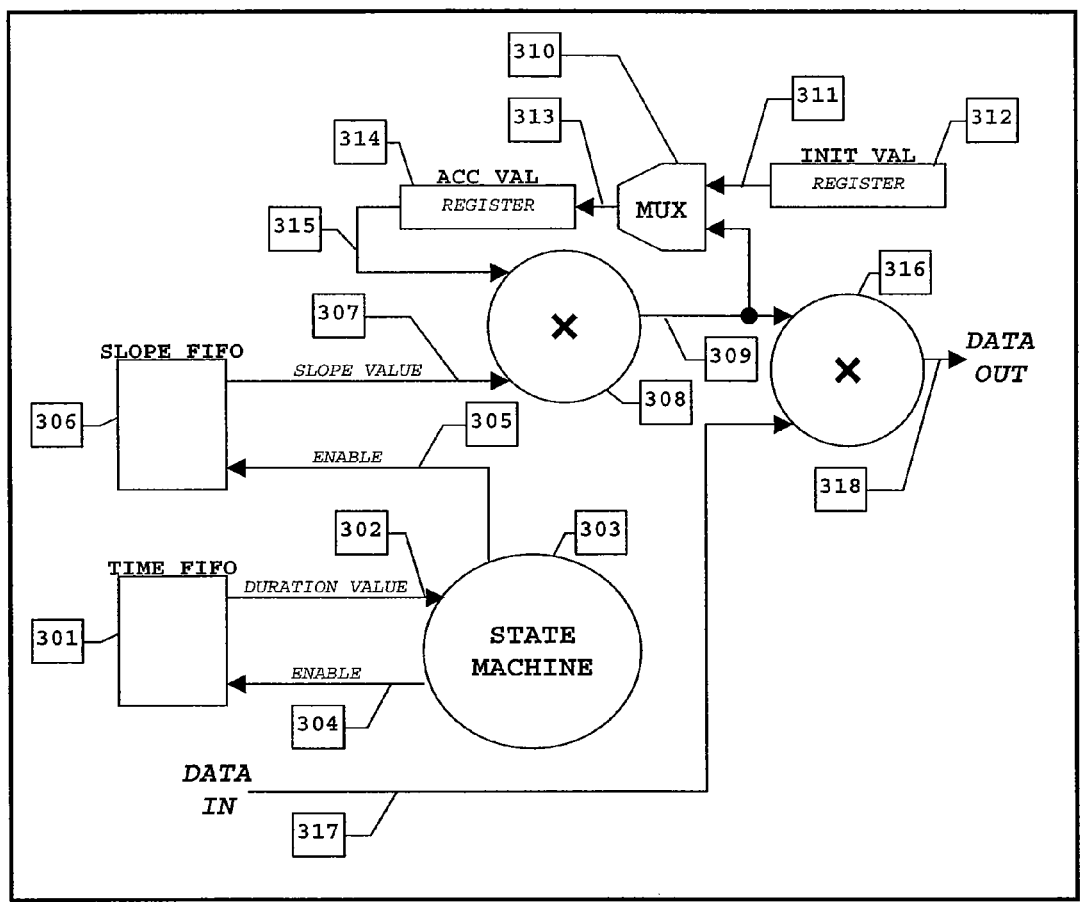

FIG. 9 illustrates one preferred implementation of the TVG 317 of the present invention. The bulk of the circuit (reference numerals 301 through 315) provides a specific scaling value 309 to the next waveform data point 317 on each SYS_CLK 342 cycle (FIG. 8a). Scaling value 309 and the sample data output from RAW_RAM 205 are multiplied together to produce the input to Averaging Decimator 206, and ultimately create the apparent gain of the signal that appears on the flaw detector waveform display 18 (FIG. 7).

It is important to note that the invention changes the TVG process. Conventional analog or digital TVG circuits use a predetermined list of gain coefficients that modify the gain at fixed time intervals. The invention uses a new TVG process that does not use fixed time intervals, and creates the gain coefficients "on-the-fly" by utilizing a slope, and duration for the slope to be applied. The circuit described in FIG. 9 is not the only way to accomplish TVG based on slope and duration. This new TVG process represents one novel concept of the invention, not the particular circuit implementation.

The system setup starts by loading a series of slope/time pairs into SLOPE FIFO 306 and TIME FIFO 301. These pairs each represent a 'gain slope'—i.e. a fixed point number ranging between 0.000008 and 1.99999 indicating the rate at which the scale factor will increase (values greater than 1) or decrease (values less than 1), and a 'duration count'—i.e. an integer value indicating the number of clock cycles to wait before advancing FIFOS 306 and 301 to the next slope/time pair.

In a time FIFO implementation, the STATE MACHINE 303 waits a set number of clock cycles, determined by DURATION VALUE 302, before incrementing both the SLOPE FIFO 306 and the TIME FIFO 301 with the ENABLE lines 304 and 305. This loads the next slope/time pair onto SLOPE VALUE 307 and DURATION VALUE 302, and the process begins again. In this way, each SLOPE VALUE 307 is driven into the first input of the MULTIPLIER 308 for the corresponding "time value" loaded into the TIME FIFO 301.

In a slope FIFO implementation, the value loaded into and driven from SLOPE FIFO 306 is an 18-bit fixed point number ranging from 0.000008 ($2^{-17}$) to 1.99999 ($2 \text{-} 2^{-17}$). This number describes the slope (rate of change over time) of SCALE FACTOR 309, resulting in the following logic:

1. values greater than 1 correspond to gain (value of scale factor 309 increases with time)
2. values less than 1 correspond to attenuation (value of scale factor 309 decreases with time)
3. a value of exactly 1 corresponds to no change (value of scale factor 309 does not change with time)

In an initial value register implementation, the SLOPE FIFO 306 and TIME FIFO 301 control how the SCALE FACTOR 309 changes with time, but the starting (initial) value of the SCALE FACTOR 309 must be preloaded into a register. This is done with the INIT VAL REGISTER 312. The MUX 310 connected in the feedback path of the MULTIPLIER 308 will load the ACC VAL REGISTER 314 with this initial value (loaded from 311) on the first cycle of the run. From then on the MUX 310 will select its other input 309 to feedback into the ACC VAL REGISTER 314.

The output of the SLOPE FIFO 306 is fed into one input of 36×36 MULTIPLIER 308, which is part of a multiplier accumulator. The second input 315 is driven from the output of the ACC VAL REGISTER 314, which contains the stored value from the last cycle. On every clock cycle, the output of MULTIPLIER 308 is fed back and loaded into this storage register 314. In this way the value stored in register (now the scale factor) 314 will adjust up or down on every clock cycle at the rate dictated by input slope value 307. It is important to note that we are using a Multiplier Accumulator to simplify the Hardware/Software interface. Using a Multiplier Accumulator utilizes slope values that are linear in decibels (dB).

In accordance with a data scaling scheme, the SCALE FACTOR 309 is sent ahead into an input of a second MULTIPLIER 316 where it is used to scale the INPUT DATA 17 point. The output of this second MULTIPLIER 316, now the scaled data, is sent out of the TVG BLOCK 317 and into the AVERAGING DECIMATOR 206.

Digital time variable gain has been done before, the difference is this method generates the gain values as they are used. Previous methods used memory chips to hold a large number of gain values that are clocked out during the receive process. This method is to be installed into an FPGA that is presumed to be part of the instrument design for other reasons. This reduces PCB board space, component costs and power requirements.

With reference to FIGS. 12 to 16, second to sixth embodiments of the TVG system are described below.

Figure 12:
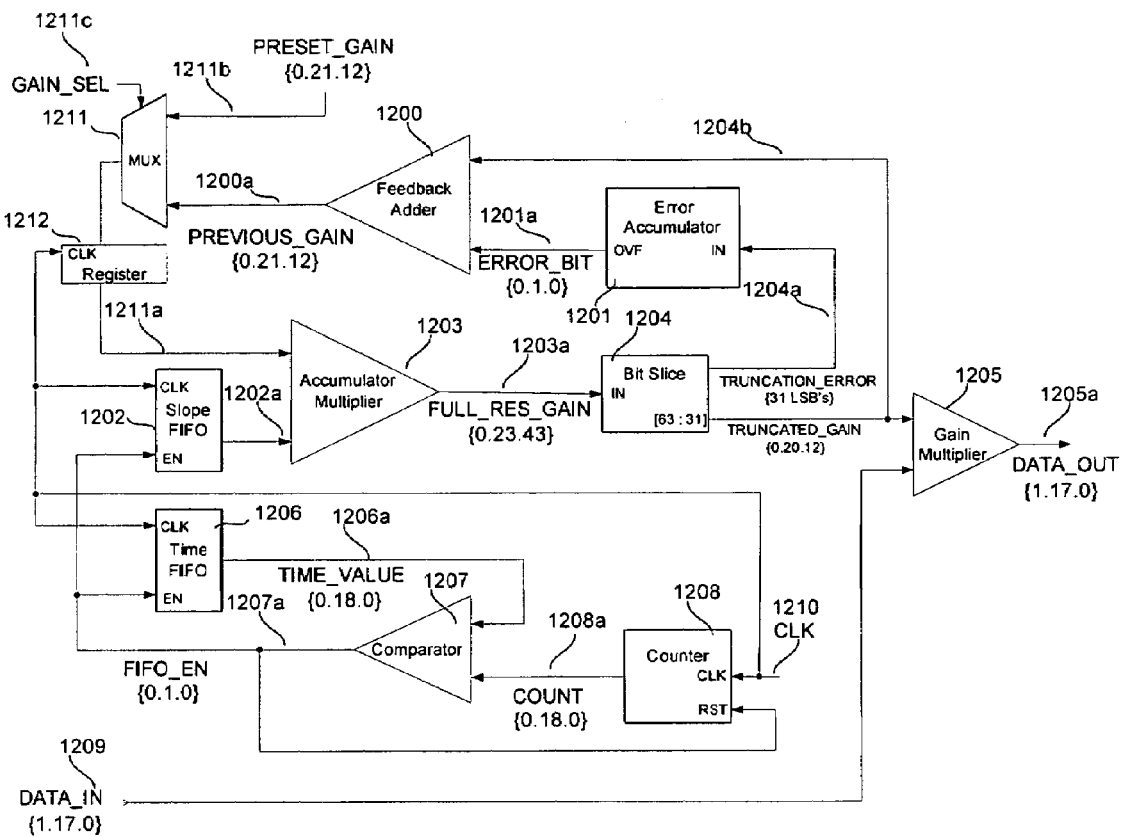

Referring first to FIG. 12 and the second embodiment, note initially the comments on terminology and formats presented immediately below.

Fixed-point labeling format: This format described below is used in FIG. 12 and in the specification for the second embodiment—i.e. this document, for now:

{number of sign bits.number of integer bits.number of fractional bits}

For example, a label of {0.1.31} would denote a fixed point number with:

32 total bits 0 sign bits (an unsigned number)

1 integer bit (a max value of 1)

31 fractional bits (a resolution of $2^{-31}$)

And a label of {1.17.0} would denote a fixed point number with:
- 18 total bits
- 1 sign bits (a signed number)
- 17 integer bits (a max value of $2^{17}-1$)
- 0 fractional bits (a resolution of 1)

In FIG. 12, Slope FIFO 1202 is used to store the TVG slope values programmed by the user to generate the desired TVG curves. Examples of slope values are shown with TVG curve 343 in FIG. 11. Each of these values will be used as the input to Accumulator Multiplier 1203 for the duration specified in its respective address in the Time FIFO 1206.

The slope values have a fixed-point format of {0.1.31}, resulting in a range from 0 to almost 2. Slope values greater than one will result in a positive slope (i.e. gain increases with each clock cycle), and values less than one will result in a negative slope (i.e. gain decreases with each clock cycle).

The slope values (SLOPE_VALUE) stored in Slope FIFO 1202 used to calculate the desired TVG curves are derived from the following equation:

$$TVG\_SLOPE = 20 * F_s * \log_{10}(SLOPE\_VALUE)$$

where,
TVG_SLOPE=gain slope in $^{dB}$/s
$F_s$=data sampling frequency in Hz
SLOPE_VALUE=the value loaded into the FIFO (0, 2)

Time FIFO 1206 is used to store the TVG duration values required to generate the desired TVG curves. Examples of slope duration values are shown with TVG curve 343 in FIG. 11 as T1 through T6. Each of these values specifies how many clock cycles to apply each corresponding slope value to the input of the Accumulator Multiplier 1203.

The duration value is an 18 bit fixed point value with format {0.18.0}, resulting in a range of 0 to $2^{18}-1$.

The slope-time pairs stored in FIFO's 1202 and 1206 respectively work in the system as targets to dead reckon from one gain to another in a specific amount of time. Each slope-time pair creates one segment of the TVG curve with a constant rate of change expressed in dB per unit time (e.g. dB/microsecond).

Counter 1208 is used to control the slope duration time interval. Counter 1208 increments by one count for each clock cycle provided to its CLK input from clock signal 1210. Output 1208a of Counter 1208 is provided to the input of Comparator 1207. Counter 1208 resets synchronously with the clock every time TIME_VALUE 1206a equals COUNT 1208a. The output value of Time FIFO 1206 and Slope FIFO 1202 also advances to the next TVG segment at this time as well. When reset, the count of Counter 1208 returns to zero.

Comparator 1207 compares the current output values of Counter 1208 and Time FIFO 1206. When the two values are equal, the output of Comparator 1207 changes state from, for example, logic zero to logic one.

Accumulator Multiplier 1203 multiplies the output of Feedback Adder 1200 by the output of Slope FIFO 1202. It should be noted that the output of Feedback Adder 1200 must be first selected by MUX 1211 and clocked into Register 1212 to accomplish this. The resulting output of Accumulator Multiplier 1203 is the full resolution gain value (FULL_RES_GAIN 1203a).

Bit Slice 1204 separates FULL_RES_GAIN 1203a into two parts and provides them as output signals 1204a and 1204b.

One part, TRUNCATION_ERROR 1204a contains only the thirty-one least significant bits of FULL_RES_GAIN 1203a and is provided to the input of Error Accumulator 1201.

The other part is TRUNCATED_GAIN 1204b which is taken from bits 31 through 63 (32 bits), using the 20 least significant integer bits and the 12 most significant fractional bits. The two most significant integer bits are dropped without substantial consequence to the system. The TRUNCATED_GAIN 1204b value is provided to the input of Feedback Adder 1200 and Gain Multiplier 1205.

Error Accumulator 1201 is a 31 bit accumulator with overflow output 1201a. It sums the TRUNCATION_ERROR 1204a on each clock cycle and sets its overflow bit high whenever the accumulated value exceeds the number that corresponds to all 31 bits being high. The overflow bit is equivalent to the LSB of the TRUNCATED_GAIN 1204b value.

Feedback Adder 1200 is a full precision adder used to add ERROR_BIT 1201a to TRUNCATED_GAIN 1204b from the feedback path. Feedback Adder 1200 generates PREVIOUS_GAIN 1200a which is provided to the input of Accumulator Multiplier 1203 by Register 1212 when it is selected as the output of Mux 1211.

Gain Multiplier 1205 multiplies DATA_IN 1209 by TRUNCATED_GAIN 1204b and removes the fractional part from the product, thereby producing a whole number for DATA_OUT 1205a.

The operation of the circuitry of FIG. 12 involves various steps as described below.

For initialization purposes, prior to the start of the TVG cycle, shown as T1 on TVG curve 343 in FIG. 11, Slope FIFO 1202 and Time FIFO 1206 are loaded with a set of slope-time pairs associated with time intervals T1 through T6 on TVG curve 343. The FIFO loading mechanism is not shown. Furthermore, PRESET_GAIN 1211b is selected as the output of Mux 1211, stored in Register 1212, the output of which is provided to the input of Accumulator Multiplier 1203, thereby setting the initial gain. The number of TVG time intervals can be more or less than six. FIG. 11 is only an example.

Next, starting and maintaining a TVG cycle is attended to. To start TVG cycle T1, clock input 1210 of Counter 1208 is enabled, causing Counter 1208 to equal the current output value of Time FIFO 1206. This in turn causes the output of Comparator 1207, FIFO_EN signal 1207a, to change state and provide a clock edge to the reset (RST) of Counter 1208, and the clock inputs of Slope FIFO 1202 and Time FIFO 1206. This clock edge causes the first pair of slope-time values of TVG curve 343 to appear on the output of Slope FIFO 1202 and Time FIFO 1206, respectively.

Concurrently, the output of Mux 1211 is switched to PREVIOUS_GAIN 1200a and Counter 1208 is reset to restart counting with each successive cycle of CLK 1210. Now that the output of Counter 1208 (COUNT) is lower than the output of Time FIFO 1206 (TIME_VALUE), Comparator 1207 changes the state of its output, FIFO_EN 1207a.

Subsequently, a TVG cycle T1 ends when the output values of Counter 1208 and Time FIFO 1206 are equal, causing Comparator 1207 to change the state of its output, FIFO_EN 1207a. This event causes Counter 1208 to be reset and the next pair of slope-time values to be provided to the output of Slope FIFO 1202 and Time FIFO 1206, respectively. The purpose of output signal 1202a of Slope FIFO 1202 will be explained in the GAIN CONTROL section below.

The FIFO Control operation described above for cycle T1 repeats for each successive cycle (T2 through T6) until all segments of TVG curve 343 are complete. It is within the purview of the second embodiment to allow PRESET_GAIN 1211b to be used as the initial gain for each successive TVG segment (T2 through T6).

The number of TVG time intervals can be more or less than six. FIG. 11 is only an example.

For gain control, PREVIOUS_GAIN 1200a is selected as the output of Mux 1211 for the following description.

On every clock cycle during a TVG interval, the output of Slope FIFO 1202 is multiplied by PREVIOUS_GAIN 1200a in Accumulator Multiplier 1203, resulting in a logarithmically adjusted FULL_RES_GAIN 1203a with each clock cycle.

FULL_RES_GAIN 1203a represents the full precision system gain at the current point in the cycle. This 66 bit value is truncated to 32 bits by Bit Slice 1204 to create TRUNCATED_GAIN signal 1204b that is provided to Feedback Adder 1200 and Gain Multiplier 1205. The 32 bit TRUNCATED_GAIN signal 1204b allows the use a narrower and less complex data path than could be achieved using all 66 bits of FULL_RES_GAIN 1203a. This benefit requires that the other output of Bit Slice 1204, TRUNCATION_ERROR 1204a, to also be properly accounted for.

A single occurrence of TRUNCATION_ERROR 1204a does not contribute a substantial error; however, an accumulation of errors over several cycles will be substantial and cause the TVG system to become inaccurate. This problem is prevented by use of Error Accumulator 1201 in conjunction with the other sub-system blocks shown in FIG. 12, and described below.

Gain output and feedback correction path proceed as follows. PREVIOUS_GAIN 1200a is selected as the output of Mux 1211 for the following description.

DATA_IN 1209 and TRUNCATED_GAIN 1204b are provided to the input of Gain Multiplier 1205 which multiplies the two to produce the output of the TVG system, DATA_OUT 1205a. Gain Multiplier 1205 truncates its output value so that the fixed point format of the output data, DATA_OUT 1205a, matches that of input data, DATA_IN 1209—specifically, the format {1.17.0}.

TRUNCATED_GAIN 1204b is also provided to one input of Feedback Adder 1200, and ERROR_BIT 1201a, from Error Accumulator 1201, is provided as the other input. Feedback Adder 1200 provides its output, PREVIOUS_GAIN 1200a, to one of the inputs of Accumulator Multiplier 1203 when it is selected as the output or Mux 1211 and loaded into Register 1212. Output 1202a of Slope FIFO 1202 is provided to the other input of Accumulator Multiplier 1203 to calculate the next gain setting.

If not compensated for, the truncation performed by BIT SLICE 1204 will produce undesirable rounding errors in the TVG curve. To mitigate this problem, Error Accumulator 1201 sums the 31 truncated bits of TRUNCATION_ERROR 1204a on every TVG clock cycle. When the 31 least significant bits from successive cycles add up to be equal to, or greater than, a 32nd bit, the Error Accumulator 1201 overflows, producing a value of one for ERROR_BIT 1201a. ERROR_BIT 1201a is then added to the value of TRUNCATED_GAIN 1204b in Feedback Adder 1200, increasing PREVIOUS_GAIN 1200a by one.

The third embodiment, which uses an analog integrator and VGA, is now described by reference to the block diagram of FIG. 13.

Figure 13:
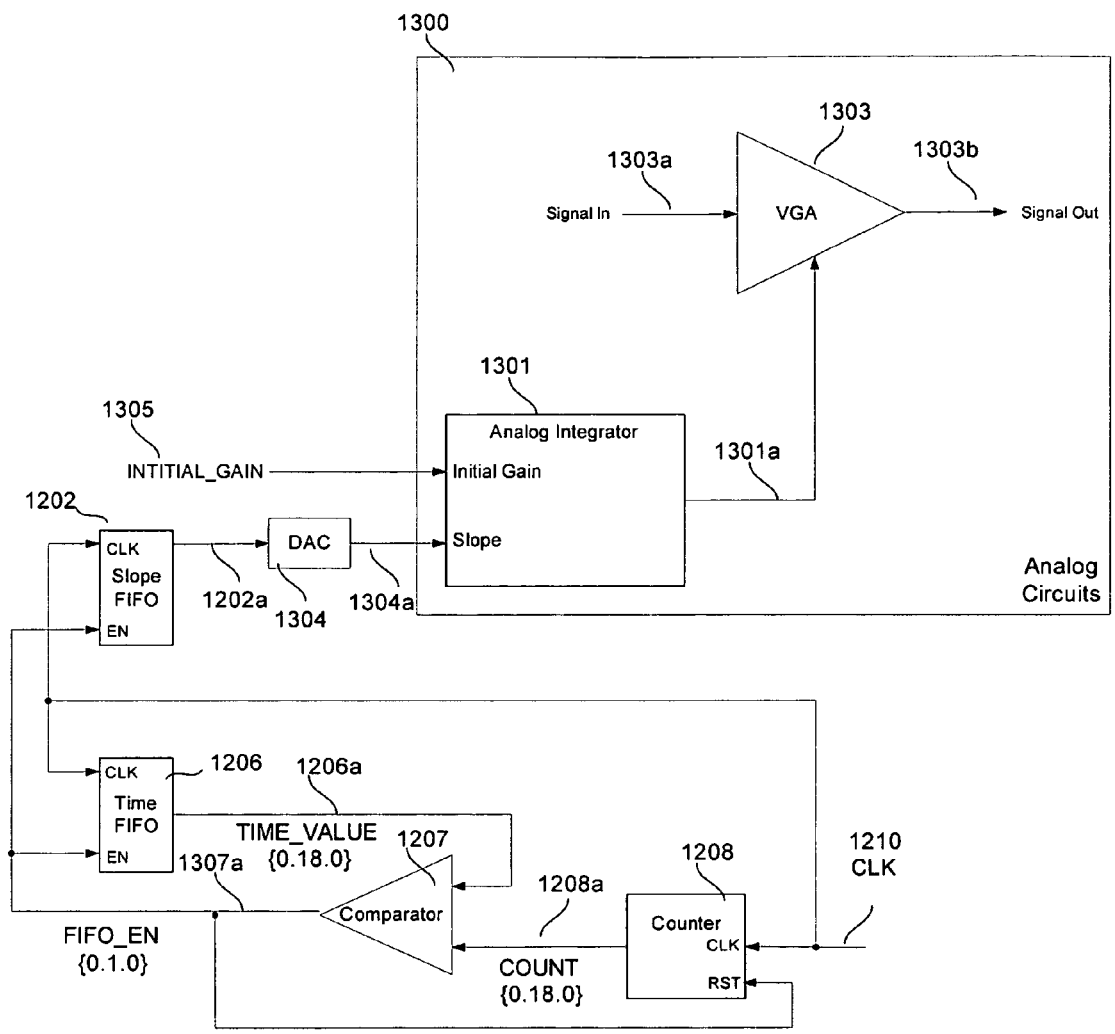

The present inventor contemplates a third embodiment that achieves the benefits of the present invention by using a combination of analog and digital circuits as shown in FIG. 13.

Specifically, the new elements of analog circuit 1300 and DAC (digital to analog converter) 1304 are used in conjunction with digital circuits 1202, 1206, 1207, 1208 and their respective signals. These digital circuits operate exactly the same way as those with corresponding item numbers in FIG. 12.

The following description refers to FIG. 13 unless otherwise noted.

For purposes of gain control, gain control for a specific TVG segment is achieved by setting the Initial Gain and Slope inputs of Analog Integrator 1301, as described below, and providing output 1301a as the gain control signal for VGA 1303. The output of Analog Integrator 1301 over the duration of the TVG segment is a DC signal with a constant slope.

The gain control function of VGA will depend on the transfer function (i.e. control voltage vs gain setting) of the component selected for VGA 1303 (e.g. linear or logarithmic). Although not shown, it is also within the purview of the invention to place a linear-to-exponential, converter in the signal path between Analog Integrator 1301 and VGA 1303 to allow either linear or logarithmic VGA's to be used.

Initialization of a TVG cycle proceeds as follows. Prior to the start of the TVG cycle, shown as T1 on TVG curve 343 in FIG. 11, Slope FIFO 1202 and Time FIFO 1206 are loaded with a set of slope-time pairs associated with time intervals T1 through T6 on TVG curve 343. The FIFO loading mechanism is not shown. The output of Slope FIFO 1202 is provided to the input of DAC 1304 to set output 1304a to a DC level that corresponds to the desired slope setting. Also as part of the initialization process, INTITAL_GAIN 1301b is provided to the input of Analog Integrator 1301 to set the initial gain.

A starting and maintaining a TVG cycle proceeds as follows. To start TVG cycle T1, clock input 1210 of Counter 1208 is enabled, causing Counter 1208 to equal the current output value of Time FIFO 1206. This in turn causes the output of Comparator 1207, FIFO_EN signal 1207a, to change state and provide a clock edge to the reset (RST) of Counter 1208, and the clock inputs of Slope FIFO 1202 and Time FIFO 1206. This clock edge causes the first pair of slope-time values of TVG curve 343 to appear on the output of Slope FIFO 1202 and Time FIFO 1206, respectively.

Concurrently, Counter 1208 is reset to restart counting with each successive cycle of CLK 1210. Now that the output of Counter 1208 (COUNT) is lower than the output of Time FIFO 1206 (TIME_VALUE), Comparator 1207 changes the state of its output, FIFO_EN 1207a. This change of state is in the opposite direction than the clock edge required to clock Slope FIFO 1202 and Time FIFO 1206; therefore, it has no affect on them.

The ending TVG cycle proceeds as follows. TVG cycle T1 ends when the output values of Counter 1208 and Time FIFO 1206 are equal, causing Comparator 1207 to change the state of its output, FIFO_EN 1207a. This event causes Counter 1208 to be reset and the next pair of slope-time values to be provided to the output of Slope FIFO 1202 and Time FIFO 1206, respectively. The purpose of output signal 1202a of Slope FIFO 1202 will be explained in the GAIN CONTROL section below.

The FIFO Control operation described above for cycle T1 repeats for each successive cycle (T2 through T6) until all segments of TVG curve 343 are complete.

The gain setting of VGA 1303 at the end of the last cycle, T6, is either maintained at a constant level or set to a new value until the next TVG curve is started. The gain is maintained at a constant level by setting the output of DAC 1304 to a slope value of zero. A new gain value is set by setting INITIAL_GAIN signal 1305 to the desired gain value, as described earlier. The new gain value can be maintained at a constant level by setting the output of DAC 1304 to a slope value of zero.

The number of TVG time intervals can be more or less than six. FIG. 11 is only an example.

The next, fourth embodiment uses a digital integrator and analog VGA is now described by reference to the block diagram of FIG. 14.

Figure 14:
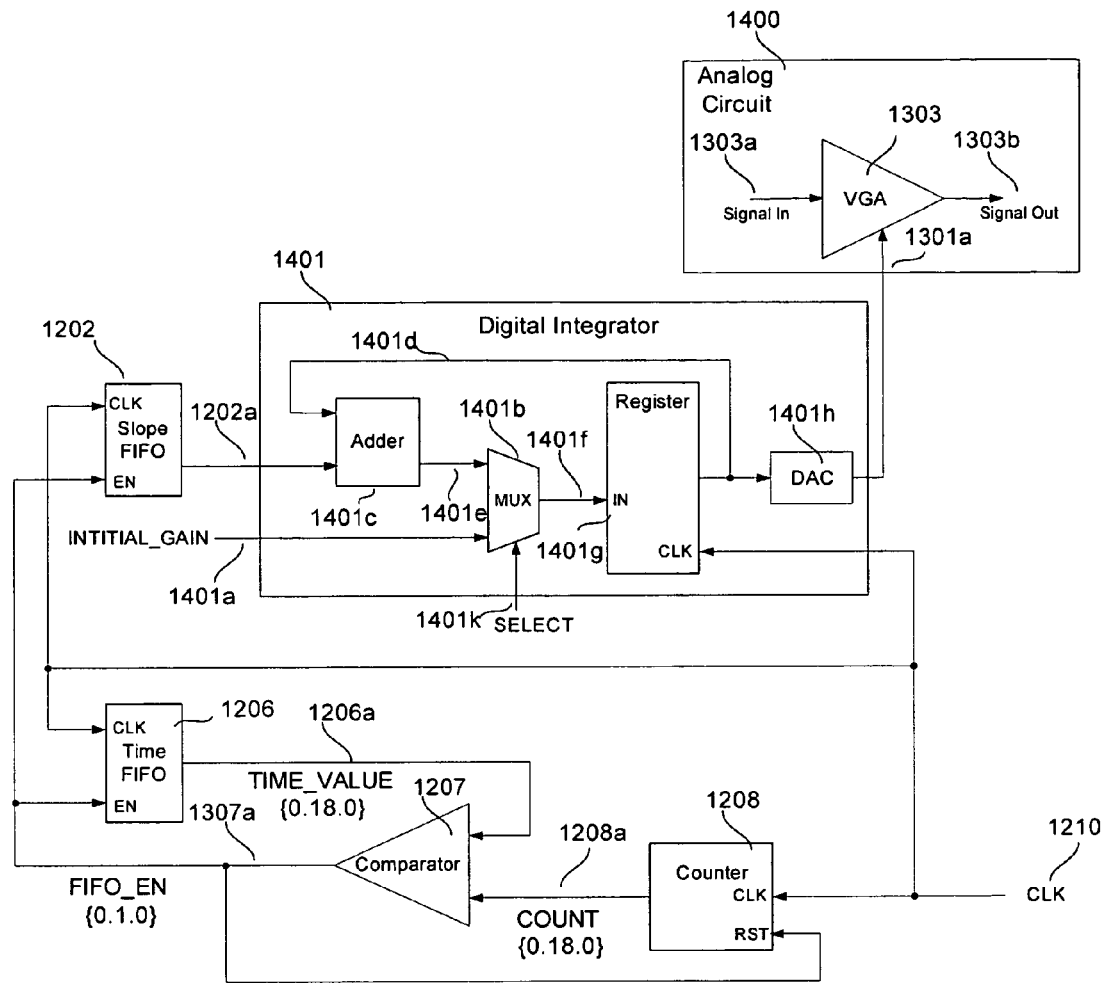

The present inventor contemplates an alternate embodiment to the third embodiment that replaces Analog Integrator 1301 and DAC 1304 shown in FIG. 13 with Digital Integrator 1401 shown in FIG. 14. The output of DAC 1401*h* is provided as the gain control signal for VGA 1400*b* to accomplish the same function as that of VGA 1303 of embodiment 3 shown in FIG. 13.

Specifically, Digital Integrator 1401 is used in conjunction with analog circuit 1400 and digital circuits 1202, 1206, 1207, 1208 and their respective signals. With the exception of Digital Integrator 1401, the digital circuits operate exactly the same way as those with corresponding item numbers in FIG. 12 of embodiment 2. Furthermore, with the exception of Analog Integrator 1301, analog circuit 1400 and its respective signals operate the same way as those with corresponding item numbers in FIG. 13.

The following description refers to FIG. 14 unless otherwise noted.

For gain control, the gain control function of VGA will be either linear or logarithmic depending on the type of component selected for VGA 1303. Although not shown, it is also within the purview of the invention to place a linear-to-exponential converter in the signal path between Register 1401*g* of Digital Integrator 1401 and VGA 1303 to allow either linear or logarithmic VGA's to be used.

Initialization of a TVG cycle proceeds as follows. Prior to the start of the TVG cycle, shown as T1 on TVG curve 343 in FIG. 11, INTIAL_GAIN signal 1401*a* is selected as the output of MUX 1401*b*, which is provided to the input of Register 1401*g*. Slope FIFO 1202 and Time FIFO 1206 are loaded with a set of slope-time pairs associated with time intervals T1 through T6 on TVG curve 343. The FIFO loading mechanism is not shown.

The number of TVG time intervals can be more or less than six. FIG. 11 is only an example.

Starting and maintaining a TVG cycle proceeds as follows. To start TVG cycle T1, clock CLK 1210 is enabled and then its first edge causes INTIAL_GAIN signal 1401*a* to be loaded to the output of Register 1401*g*, thereby setting the output of DAC 1401*h* to the desired initial gain of VGA 1303. At the same time, Output 1401*d* of Register 1401*g* is also provided to the input of Adder 1401*c* and Counter 1208 is incremented to one count above the current output value of Time FIFO 1206. This in turn causes the output of Comparator 1207, FIFO_EN signal 1207*a*, to change state, thereby resetting Counter 1208 and starting TVG cycle T1. This change of state of FIFO_EN signal 1207*a* also clocks Slope FIFO 1202 and Time FIFO 1206 causing the first pair of slope-time values of TVG curve 343 to appear on there outputs, respectively. It also causes the output of Counter 1208 (COUNT) to be lower than the output of Time FIFO 1206 (TIME_VALUE) causing Comparator 1207 to change the state of its output, FIFO_EN 1207*a*, in preparation for the reset event that causes the end of TVG cycle T1. This change of state is in the opposite direction than the clock edge required to clock Slope FIFO 1202 and Time FIFO 1206, and reset CLK 1210; therefore, it has no affect on them because is not a clocking edge.

Any time after the first clock edge of CLK 1210 and before the start of its next cycle, the output of Adder 1401*c* is selected by MUX 1401*b* and provided to the input of Register 1401*g*. This input is transferred to the output of Register 1401*g* at the start of the next cycle of CLK 1210, thereby creating the next gain setting after the initial gain value. At this time, the output of Register 1401*g* contains a gain value which is the sum of INITIAL_GAIN signal 1401*a* and the first slope value from Slope FIFO 1202. This output is provided to the input of DAC 1401*h* to produce gain control signal 1301*a* for VGA 1303.

Depending on the polarity of the slope value provided by Slope FIFO 1202, gain control signal 1301*a* will either increment or decrement the gain of VGA 1303 on each successive clock cycle of CLK1210. If the slope polarity is positive, the gain change is equal to the previous gain plus the magnitude of the slope value. If the slope polarity is negative, the gain change is equal to the previous gain minus the magnitude of the slope value. This process continues until the end of segment T1, and repeats for segments T2 through T6 on TVG curve 343 shown in FIG. 11.

Segments T2 through T6 on TVG curve 343 are started when the next clocking edge of FIFO_EN signal 1207*a* transfers the next set of values of Slope FIFO 1202 and Time FIFO 1206 to their respective outputs. Furthermore, the output of Register 1401*g* is loaded with a gain value equal to the sum of the gain of the preceding cycle and the second slope value of Slope FIFO 1202. This output is provided to the input of DAC 1401*h* to produce signal 1301*a* that is provided to the gain control pin of VGA 1303. This process continues until the end of the TVG curve 343.

The procedure for ending a TVG cycle is as follows. Each TVG cycle (T1 through T6) ends when the output values of Counter 1208 and Time FIFO 1206 are equal, causing Comparator 1207 to change the state of its output, FIFO_EN 1207*a*. This event causes Counter 1208 to be reset and the next pair of slope-time values to be provided to the output of Slope FIFO 1202 and Time FIFO 1206, respectively.

The gain setting of VGA 1303 at the end of the last cycle, T6, is either maintained or set to a new value until the next TVG curve is started. One way to maintain a constant gain is by disabling CLK 1210. One way to set a new gain value is by using INITIAL_GAIN signal 1401*a* as described earlier.

The number of TVG time intervals can be more or less than six. FIG. 11 is only an example.

The next, fifth embodiment uses a digital integrator and gain multiplier to achieve piece-wise linear TVG curves, and is described below by reference to the block diagram of FIG. 15.

The fifth embodiment operates exactly the same way as the fourth embodiment except DAC 1401*h* and VGA 1303 are removed and the output of Register 1401*g* is provided to Gain Multiplier 1500. Furthermore, because this is a purely digital implementation, DATA_IN 1209 is provided to the input of Gain Multiplier 1500 and DATA_OUT is its output.

The fifth embodiment differs in that although the gain control is a linear function, logarithmic TVG curve 343 of FIG. 11 can be approximated using a piece-wise linear method if the number of points on each T segment of the TVG curve is sufficient.

The sixth, embodiment uses a digital integrator, linear to exponential converter, and gain multiplier to achieve logarithmic TVG curves, and is described next by reference to the block diagram of FIG. 16.

The sixth embodiment operates exactly the same way as the fifth embodiment, except for linear to exponential converter 1600 being inserted between the output of Register 1401*g* and the input to Gain Multiplier 1500. This allows the linear output of Register 1401*g* to generate a logarithmic TVG curve.

Figure 15:
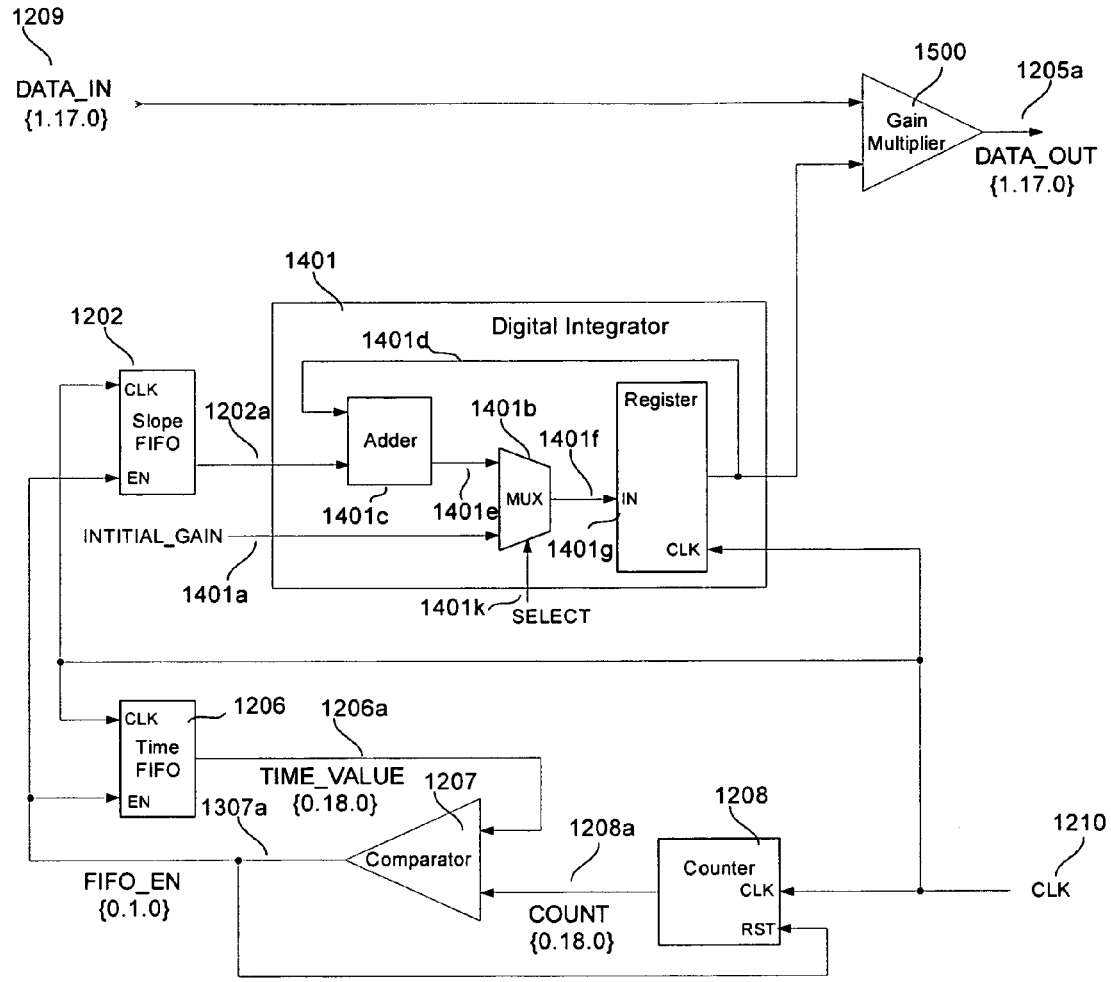
Figure 16:
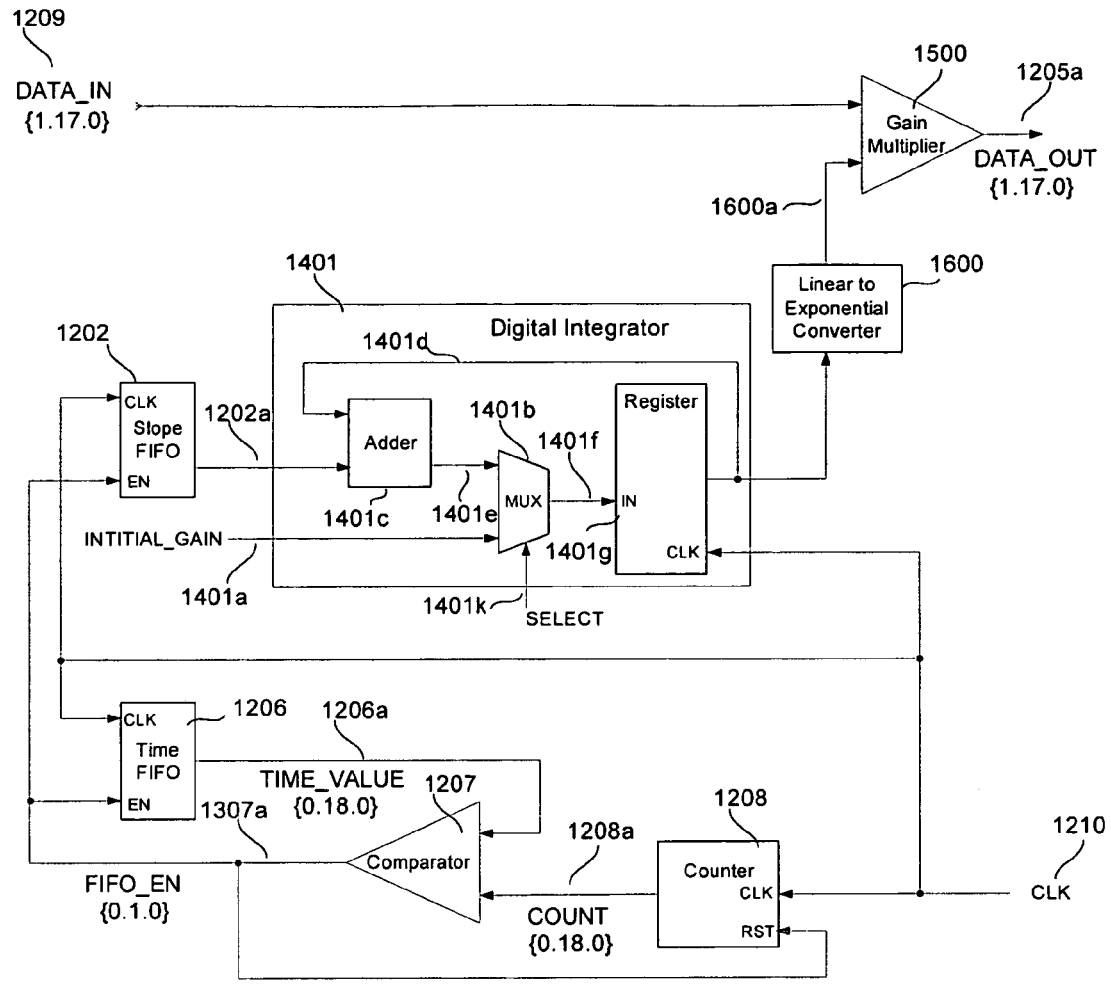

It should also be noted that the following scenarios are also within the purview of the invention:

a) Digital Integrator using piece-wise linear approximation of a logarithmic TVG function with a linear controlled analog TVG b) Output 1301a of Analog Integrator 1301 of FIG. 13 is sampled with an A/D converter (not shown), the output of which is used to replace the output of the Digital Integrator 1401 shown in FIGS. 15 and 16.

Throughout the specification and claims, reference is made to "echo" signals. As will be appreciated by people of skill in the art, in certain environments or applications, the transmitter and receiver components of the transducer 12 are physically separated, with the receiver being located on an opposite side of the object being tested. Hence, the term "echo" as used herein also pertains and encompasses embodiments where the so-called echo signal passes through the object being tested.

In the preceding description, the invention that has been described exclusively with respect to embodiments wherein flaw detection is carried out with a single transducer element operating exclusively under the echo principle and/or by reference to a transmitter/receiver pair which handle ultrasound waves that pass through a material. However, it should be noted the present invention is equally applicable to flaw detection instruments that use an array of transducer elements, such as an ultrasonic phased array probe. As is the case with a single element ultrasonic transducer, the response signal for each transducer element of the phased array ultrasonic probe used for reception is provided to the input of a receiver channel for conditioning and subsequent digitization by an analog to digital converter. In other words, the reference in the claims to a "transducer"—in the singular—is deemed to pertain to an ultrasonic phased array type of a probe as well. Such arrays of transducers are deemed to be either identical or at least equivalent to a single element transducer. The structure of such ultrasonic phased array devices is described or referenced in U.S. Pat. Nos. 4,497,210 and 6,789,427, the contents of which patents are incorporated herein by reference.

Although the present invention has been described in relation to particular embodiments thereof, many other variations and modifications and other uses will become apparent to those skilled in the art. It is preferred, therefore, that the present invention be limited not by the specific disclosure herein, but only by the appended claims.

What is claimed is:

1. A time variable gain circuit, comprising:
   an input circuit for receiving an input signal;
   a first circuit for storing a plurality of slope duration values;
   a second circuit for storing slope data applicable for respective ones of said slope duration values;
   a third circuit for storing an initial gain value;
   a control circuit, responsive to said slope duration values, said slope data, and said initial gain value, to generate therewith a scaling function applicable to said input signal; and
   a scaling circuit for receiving said input signal and processing said input signal with the scaling function generated by the control circuit.

2. The circuit of claim 1, wherein said input signal is an analog signal and wherein said scaling circuit produces an analog output.

3. The circuit of claim 1, wherein said control circuit is operative to set a constant slope value for each corresponding slope duration value based on a respective slope value associated with the corresponding slope duration value.

4. The circuit of claim 3, wherein the difference between the start scaling value and the end scaling value is different for different ones of said slope duration values.

5. The circuit of claim 1, wherein each of the first and second circuits comprises a respective FIFO.

6. The circuit of claim 1, wherein the scaling function is a number that when multiplied with an input signal causes the input signal to increase, decrease or remain the same.

7. The circuit of claim 1, including an accumulator circuit for producing time-wise varying scaling values which comprise the scaling function.

8. The circuit of claim 7, wherein the scale function produces scaling values which can be varied in as little as ten nanoseconds.

9. The circuit of claim 7, wherein the accumulator multiplier produces scaling values that vary linearly in decibels.

10. The circuit of claim 1, further comprising a multiplexer to initially select the initial gain value.

11. The circuit of claim 1, wherein said circuit is implemented substantially entirely of digital circuitry.

12. The circuit of claim 1, wherein parameters of the scaling function are dynamically changeable.

13. The circuit of claim 1, wherein the slope data is variable from $0.000008(2^{-17})$ to $1.99999(2-2^{-17})$.

14. The circuit of claim 1, in combination with an ultrasonic system for scanning objects to be tested.

15. The circuit of claim 14, wherein the ultrasonic detection system comprises:
   a transmit and receive device to generate a test signal and to receive a responsive echo signal;
   a transducer that converts the test signal to an ultrasonic signal, applies the ultrasonic signal to a target object to be tested, receives an ultrasonic echo signal and produces the echo signal for the transmit and receive device;
   a signal processing circuit coupled with the transmit and receive device for receiving and processing the echo signal, the signal processing circuit including at least one digital to analog converter for converting an analog version of the echo signal to a digital echo signal comprising streaming digital data;
   a memory in which the streaming data is received at a data rate;
   an infinite impulse response (IIR) filter that operates on data received from the digital time variable gain circuit and provides an output data to a finite impulse response (FIR) filter for applying a band pass function to the data; and
   a box car filter which interpolates the data received from the FIR filter in a manner which increases the perceived resolution of the data.

16. The circuit of claim 15, further including an averaging decimator coupled with the time variable gain circuit.

17. The system of claim 15, wherein the FIR filter is set to provide a frequency selectivity response which provides a −6 dB low pass filter point which is less than 10% of a filter clock applied thereto.

18. The system of claim 15, wherein a clock rate associated with the memory read out function is one fourth a clock rate of the analog to digital converter.

19. The system of claim 15, wherein the FIR filter is a MAC filter with 32 coefficients.

20. The system of claim 15, wherein the FIR filter is set to provide the function of a low pass filter.

21. The system of claim 15, wherein a −6 dB setting for the FIR filter is selectable in the range from about 0.1 to about 25 MHz.

22. The circuit of claim 1, including an error accumulator structured to note a cumulative error in the scaling function and to apply a correction value to correct for the accumulated error.

23. The circuit of claim 22, wherein each of the first and second circuit comprises a respective FIFO, and including an accumulator multiplier responsive to the second circuit and to a signal derived from the error accumulator, and including a bit slice circuit having a gain output and a truncation error output.

24. The circuit of claim 23, including a gain multiplier which is responsive to the gain output of said bit slice circuit and to input data which is based on said input signal.

25. The circuit of claim 24, wherein the input data is presented as a fixed point number having three segments, including a number of sign bits segment, a number of integer bits segment and a number of fractional bits segment.

26. The circuit of claim 25, including a circuit clock and wherein the circuit is structured to update the scaling value on each clock cycle of the circuit clock.

27. The circuit of claim 1, wherein the scaling function is represented by a variable TVG_SLOPE which is defined as:

$$TVG\_SLOPE = 20 * F_s * \log_{10}(SLOPE\_VALUE)$$

where,
TVG_SLOPE=gain slope in $dB/s$
$F_s$=data sampling frequency in Hz
SLOPE_VALUE=the value loaded into the FIFO (0, 2).

28. The circuit of claim 1, wherein the scaling function is represented by digital slope values and further including a digital to analog converter responsive to the digital slope values and having an analog slope output, and further including an analog integrator responsive to the analog slope output and operable to output an analog scaling function.

29. The circuit of claim 28, further comprising a variable gain amplifier responsive to the analog slope function and to the input signal to produce an analog signal output.

30. The circuit of claim 1, further including a digital integrator responsive to said second circuit and structured to produce said scaling function in the form of digital scaling values.

31. The circuit of claim 30, further including a digital to analog converter operable for converting said digital scaling values to an analog scaling function, and further including an analog variable gain amplifier responsive to said analog scaling function and to said input signal.

32. The circuit of claim 30, further including a digital, variable gain multiplier responsive to said digital scaling values and to a digital signal derived from said input signal.

33. The circuit of claim 32, further including a linear to exponential converter coupled between said digital integrator and said digital, variable gain multiplier.

34. The circuit of claim 30, wherein said digital integrator is structured to produce a piece-wise linear approximation of a logarithmic TVG function utilizing a linear-controlled analog TVG.

35. The circuit of claim 30, wherein said analog integrator is structured to be sampled with an analog to digital converter the output of which is supplied to a digital gain multiplier which is also responsive to a digital signal derived from said input signal.

* * * * *